(12) United States Patent
Furneaux et al.

(10) Patent No.: US 6,492,347 B2
(45) Date of Patent: Dec. 10, 2002

(54) INHIBITORS OF NUCLEOSIDE METABOLISM

(75) Inventors: Richard Hubert Furneaux, Wellington (NZ); Peter Charles Tyler, Wellington (NZ); Vern L. Schramm, New Rochelle, NY (US)

(73) Assignees: Albert Einstein College of Medicine of Yeshiva University, Bronx, NY (US); Industrial Research Limited, Lower Hutt (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 09/820,276

(22) Filed: Mar. 28, 2001

(65) Prior Publication Data

US 2002/0061898 A1 May 23, 2002

Related U.S. Application Data

(63) Continuation of application No. 09/496,741, filed on Feb. 3, 2000, now Pat. No. 6,228,847, which is a continuation of application No. 09/172,321, filed on Oct. 14, 1998, now Pat. No. 6,066,722, which is a continuation-in-part of application No. 08/949,388, filed on Oct. 14, 1997, now Pat. No. 5,985,848.

(51) Int. Cl.$^7$ .............................. A01N 43/04
(52) U.S. Cl. ....................................... 514/44
(58) Field of Search ..................... 514/44, 1; 536/22.1, 536/4.1, 23.1, 25.3

(56) References Cited

U.S. PATENT DOCUMENTS 5,985,848 A * 11/1999 Furneaux et al. ............. 514/44

* cited by examiner

Primary Examiner—Jezia Riley
(74) Attorney, Agent, or Firm—Amster, Rothstein & Ebenstein

(57) ABSTRACT

The present invention provides novel nucleoside-analogue compounds that are effective inhibitors of purine nucleoside phosphorylase (PNP), purine phosphoribosyltransferases (PPRT), and/or nucleoside hydrolases. Also provided are tautomers, esters, prodrugs, and pharmaceutically-acceptable salts of the compounds disclosed herein. The present invention further provides the use of these compounds as pharmaceuticals. The present invention also discloses pharmaceutical compositions containing these compounds. Finally, the present invention provides processes for preparing these compounds.

2 Claims, 8 Drawing Sheets

INHIBITORS OF NUCLEOSIDE METABOLISM

CROSS REFERENCE TO RELATED APPLICATIONS

This is a continuation of U.S. application Ser. No. 09/496,471, filed Feb. 3, 2000, now U.S. Pat. No. 6,228,847, which is a continuation of U.S. application Ser. No. 09/172,321, filed Oct. 14, 1998, now U.S. Pat. No. 6,066,722, which is a continuation-in-part of U.S. application Ser. No. 08/949,388, filed Oct. 14, 1997, now U.S. Pat. No. 5,985,848, the contents of which are hereby incorporated by reference in their entirety.

TECHNICAL FIELD

The invention relates to certain nucleoside analogues, the use of these compounds as pharmaceuticals, pharmaceutical compositions containing the compounds and processes for preparing the compounds.

BACKGROUND OF THE INVENTION

Purine nucleoside phosphorylase (PNP) catalyses the phosphorolytic cleavage of ribo- and deoxyribonucleosides, for example, those of guanine and hypoxanthine to give the corresponding sugar-1-phosphate and guanine, hypoxanthine, or other purine bases.

Humans deficient in purine nucleoside phosphorylase (PNP) suffer a specific T-cell immunodeficiency due to an accumulation of dGTP and its toxicity to stimulated T lymphocytes. Because of this, inhibitors against PNP are immunosuppressive, and are active against T-cell malignancies. Clinical trials are now in progress using 9-(3-pyridylmethyl)-9-deazaguanine in topical form against psoriasis and in oral form for T-cell lymphoma and immunosuppression (BioCryst Pharmaceuticals, Inc). The compound has an $IC_{50}$ of 35 nM for the enzyme. In animal studies, a 50 mg/kg oral dose is required for activity in a contact sensitivity ear swelling assay in mice. For human doses, this would mean approximately 3.5 grams for a 70 kg human. With this inhibitor, PNP is difficult to inhibit due to the relatively high activity of the enzyme in blood and mammalian tissues.

Nucleoside and deoxynucleoside hydrolases catalyse the hydrolysis of nucleosides and deoxynucleosides. These enzymes are not found in mammals but are required for nucleoside salvage in some protozoan parasites. Purine phosphoribosyltransferases (PPRT) catalyze the transfer of purine bases to 5-phospho-α-D-ribose-1-pyrophosphate to form purine nucleotide 5'-phosphates. Protozoan and other parasites contain PPRT which are involved in essential purine salvage pathways. Malignant tissues also contain PPRT. Some protozoan parasites contain purine nucleoside phosphorylases which also function in purine salvage pathways. Inhibitors of nucleoside hydrolases, purine nucleoside phosphorylases and PPRT can be expected to interfere with the metabolism of parasites and therefore be usefully employed against protozoan parasites. Inhibitors of PNP and PPRT can be expected to interfere with purine metabolism in malignant tissues and therefore be usefully employed against malignant tissues.

It is an object of the invention to provide pharmaceuticals which are very effective inhibitors of PNP, PPRT and/or nucleoside hydrolases.

BRIEF DESCRIPTION OF THE FIGURES

FIG. 1 shows purine nucleoside phosphorylase activity with time at a range of concentrations of the product of Example 1 (Compound Ib).

FIG. 2 shows fitting of a purine nucleoside phosphorylase activity progress curve to the kinetic model.

FIG. 3 shows $K_i^*$ determination by the curve fit method for Compound Ib inhibition of bovine purine nucleoside phosphorylase.

FIG. 4 shows a progress curve for bovine purine nucleoside phosphorylase showing slow-onset inhibition by Compound Ib.

FIGS. 5A–5C shows the effect of oral administration of Compound Ib on the PNP activity of mouse blood.

FIGS. 6A–6C: FIGS. 6A–6B shows the $K_i$ determination for Compound Ib with protozoan nucleoside hydrolase.

FIG. 7 shows the progress curve for purine phosphoribosyltransferase showing slow-onset inhibition by the 5'-phosphate of Compound Ib. Inhibition of the malaria enzyme.

FIG. 8 shows the $K_1^*$ determination for the 5'-phosphate of Compound Ib inhibition of human purine phosphoribosyltransferase.

DETAILED DESCRIPTION OF THE INVENTION

Figure 1:
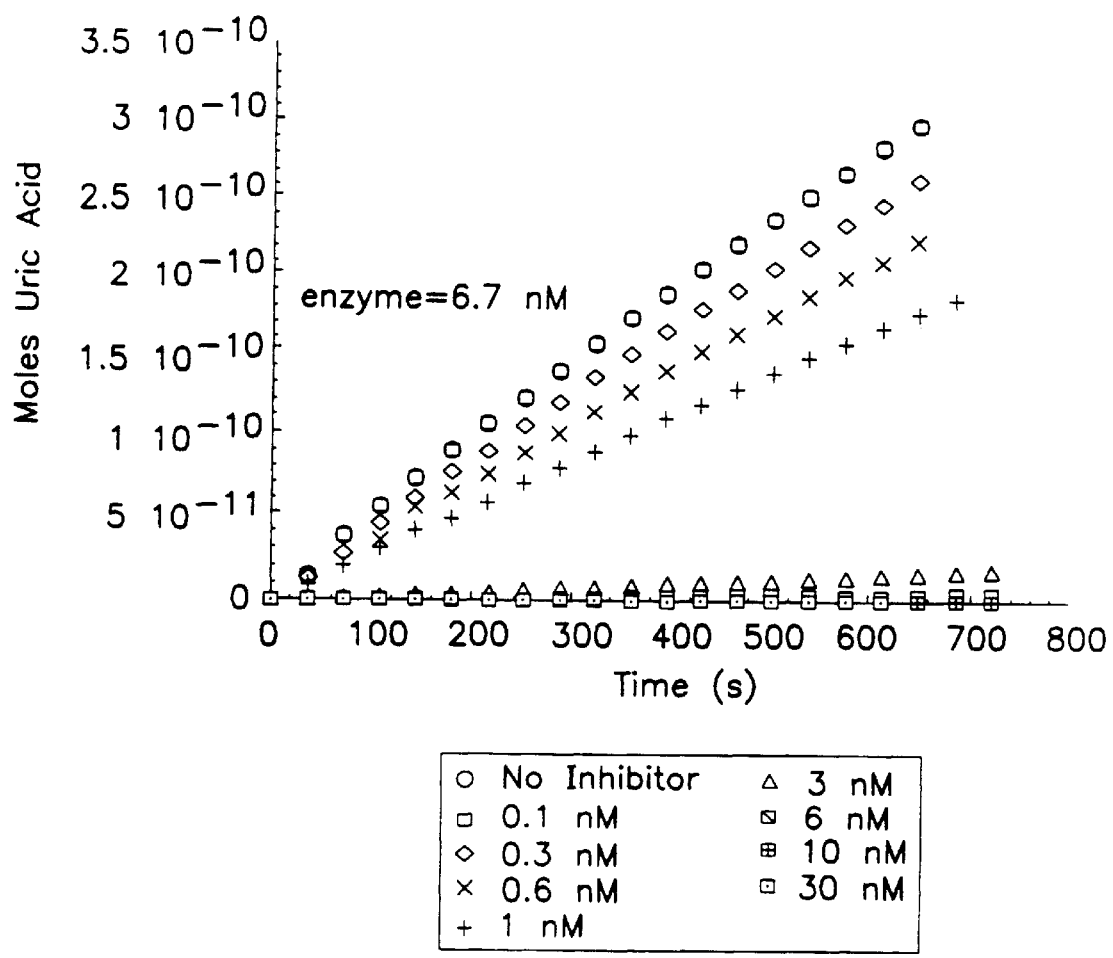
FIG. 1.

In one aspect the invention provides compounds having the formula:

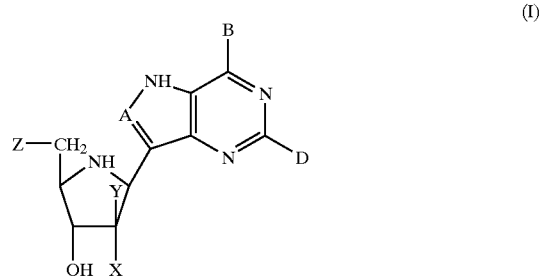

wherein A is CH or N; B is chosen from OH, $NH_2$, NHR, H or halogen; D is chosen from OH, $NH_2$, NHR, H, halogen or $SCH_3$; R is an optionally substituted alkyl, aralkyl or aryl group; and X and Y are independently selected from H, OH or halogen except that when one of X and Y is hydroxy or halogen, the other is hydrogen; and Z is OH or, when X is hydroxy, Z is selected from hydrogen, halogen, hydroxy, SQ or OQ, Q is an optionally substituted alkyl, aralkyl or aryl group; or a tautomer thereof; or a pharmaceutically acceptable salt thereof; or an ester thereof; or a prodrug thereof.

Preferably when either of B and/or D is NHR, then R is $C_1$–$C_4$ alkyl.

Preferably when one or more halogens are present they are chosen from chlorine and fluorine.

Preferably when Z is SQ or OQ, Q is $C_1$–$C_5$ alkyl or phenyl.

Preferably D is H, or when D is other than H, B is OH.

More preferably, B is OH, D is H, OH or $NH_2$, X is OH or H, Y is H, most preferably with Z as OH, H or methylthio, especially OH.

It will be appreciated that the representation of a compound of formula (I) wherein B and/or D is a hydroxy group used herein is of the enol-type tautomeric form of a corresponding amide, and this will largely exist in the amide form. The use of the enol-type tautomeric representation is simply to allow fewer structural formulae to represent the compounds of the invention.

The present invention also provides compounds having the formula:

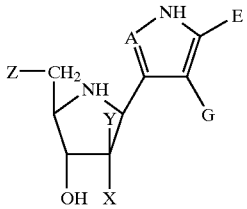

(Ia)

wherein A, X, Y, Z and R are defined for compounds of formula (I) where first shown above; E is chosen from $CO_2H$ or a corresponding salt form, $CO_2R$, CN, $CONH_2$, CONHR or $CONR_2$; and G is chosen from $NH_2$, NHCOR, NHCONHR or NHCSNHR; or a tautomer thereof, or a pharmaceutically acceptable salt thereof, or an ester thereof, or a prodrug thereof.

Preferably E is $CONH_2$ and G is $NH_2$.

More preferably, E is $CONH_2$, G is $NH_2$, X is OH or H, is H, most preferable with Z as OH, H or methylthio, especially OH.

Particularly preferred are the following compounds:
1. (1S)-1,4-dideoxy-1-C-(4-hydroxypyrrolo[3,2-d]pyrimidin-7-yl)-1,4-imino-D-ribitol
2. (1S)-1-C-(2-amino-4-hydroxypyrrolo[3,2-d]pyrimidin-7-yl)-1,4-dideoxy-1,4-imino-D-ribitol
3. (1R)-1-C-(4-hydroxypyrrolo[3,2-d]pyrimidin-7-yl)-1,4-imino-1,2,4-trideoxy-D-erythro-pentitol
4. (1S)-1-C-(4-hydroxypyrrolo[3,2-d]pyrimidin-7-yl)-1,4-imino-1,4,5-trideoxy-D-ribitol
5. (1S)-1,4-dideoxy-1-C-(4-hydroxypyrrolo[3,2-d]pyrimidin-7-yl)-1,4-imino-5-methylthio-D-ribitol
6. (1S)-1,4-dideoxy-1-C-(2,4-dihydroxypyrrolo[3,2-d]pyrimidin-7-yl)-1,4-imino-D-ribitol
7. (1R)-1-C-(2,4-dihydroxypyrrolo[3,2-d]pyrimidin-7-yl)-1,4-imino-1,2,4-trideoxy-D-erthro-pentitol
8. (1S)-1-C-(2,4-dihydroxypyrrolo[3,2-d]pyrimidin-7-yl)-1,4-imino-1,4,5-trideoxy-D-ribitol
9. (1S)-1,4-dideoxy-1-C-(2,4-dihydroxypyrrolo[3,2-d]pyrimidin-7-yl)-1,4-imino-5-methylthio-D-ribitol
10. (1R)-1-C-(2-amino-4-hydroxypyrrolo[3,2-d]pyrimidin-7-yl)-1,4-imino-1,2,4-trideoxy-D-erythro-pentitol
11. (1S)-1-C-(2-amino-4-hydroxypyrrolo[3,2-d]pyrimidin-7-yl)-1,4-imino-1,4,5-trideoxy-D-ribitol
12. (1S)-1-C-(2-amino-4-hydroxypyrrolo[3,2-d]pyrimidin-7-yl)-1,4-dideoxy-1,4-imino-5-methylthio-D-ribitol
13. (1S)-1,4-dideoxy-1-C-(7-hydroxypyrazolo[4,3-d]pyrimidin-3-yl)-1,4-imino-D-ribitol
14. (1R)-1-C-(7-hydroxypyrazolo[4,3-d]pyrimidin-3-yl)-1,4-imino-1,2,4-trideoxy-D-erythro-pentitol
15. (1S)-1-C-(7-hydroxypyrazolo[4,3-d]pyrimidin-3-yl)-1,4-imino-1,4,5-trideoxy-D-ribitol
16. (1S)-1,4-dideoxy-1-C-(7-hydroxypyrazolo[4,3-d]pyrimidin-3-yl)-1,4-imino-5-methylthio-D-ribitol
17. (1S)-1,4-dideoxy-1-C-(5,7-dihydroxypyrazolo[4,3-d]pyrimidin-3-yl)-1,4-imino-D-ribitol
18. (1R)-1-C-(5,7-dihydroxypyrazolo[4,3-d]pyrimidin-3-yl)-1,4-imino-1,2,4-trideoxy-D-erythro-pentitol
19. (1S)-1-C-(5,7-dihydroxypyrazolo[4,3-d]pyrimidin-3-yl)-1,4-imino-1,4,5-trideoxy-D-ribitol
20. (1S)-1,4-dideoxy-1-C-(5,7-dihydroxypyrazolo[4,3-d]pyrimidin-3-yl)-1,4-imino-5-methylthio-D-ribitol
21. (1S)-1-C-(5-amino-7-hydroxypyrazolo[4,3-d]pyrimidin-3-yl)-1,4-dideoxy-1,4-imino-D-ribitol
22. (1R)-1-C-(S-amino-7-hydroxypyrazolo[4,3-d]pyrimidin-3-yl)-1,4-imino-1,2,4-trideoxy-D-erythro-pentitol
23. (1S)-1-C-(5-amino-7-hydroxypyrazolo[4,3-d]pyrimidin-3-yl)-1,4-imino-1,4,5-trideoxy-D-ribitol
24. (1S)-1-C-(5-amino-7-hydroxypyrazolo[4,3-d]pyrimidin-3-yl)-1,4-dideoxy-1,4-imino-5-methylthio-D-ribitol
25. (1S)-1-C-(3-amino-2-carboxamido-4-pyrroly)-1,4-dideoxy-1,4-imino-D-ribitol.
26. (1S)-1,4-dideoxy-1-C-(4-hydroxypyrrolo[3,2-d]pyrimidin-7-yl)-1,4-imino-D-ribitol 5-phosphate
27. (1S)-1-C-(2-amino-4-hydroxypyrrolo[3,2-d]pyrimidin-7-yl)-1,4-imino-D-ribitol 5-phosphate
28. (1S)-1-C-(3-amino-2-carboxamido-4-pyrrolyl)-1,4-dideoxy-1,4-imino-D-ribitol Most preferred are compounds Ib and Ic, their tautomers and pharmaceutically acceptable salts.

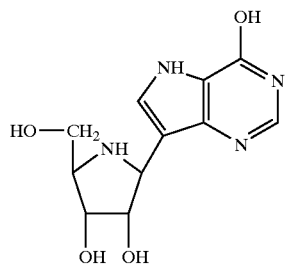

Ib

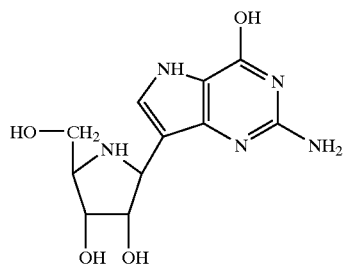

Ic

The biological availability of a compound of formula (I) or formula (Ia) can be enhanced by conversion into a pro-drug form. Such a pro-drug can have improved lipophilicity relative to the compound of formula (I) or formula (Ia), and this can result in enhanced membrane permeability. One particularly useful form of a pro-drug is an ester derivative. Its utility relies upon the action of one or more of the ubiquitous intracellular lipases to catalyse the hydrolysis of these ester group(s), to release the compound of formula (I) and formula (Ia) at or near its site of action.

In one form of a prodrug, one or more of the hydroxy groups in a compound of formula (I) or formula (Ia) can be O-acylated, to make, for example a 5-O-butyrate or a 2,3-di-O-butyrate derivative.

Prodrug forms of 5-phosphate ester derivative of a compounds of formula (I) or formula (Ia) can also be made and may be particularly useful, since the anionic nature of the 5-phosphate may limit its ability to cross cellular membranes. Conveniently, such a 5-phosphate derivative can be converted to an uncharged bis(acyloxymethyl) ester derivative. The utility of such a pro-drug relies upon the action of one or more of the ubiquitous intracellular lipases to catalyse the hydrolysis of these ester group(s), releasing a molecule of formaldehyde and the compound of formula (I) or formula (Ia) at or near its site of action.

Specific examples of the utility of, and general methods for making, such acyloxymethyl ester pro-drug forms of phosphorylated carbohydrate derivatives have been described, e.g. Kang et al., *Nucleosides Nucleotides* 17 (1998) 1089; Jiang et al., *J. Biol. Chem.*, 273 (1998) 11017; Li et al., *Tetrahedron* 53 (1997) 12017; and Kruppa et al., *Bioorg. Med. Chem. Lett.*, 7 (1997) 945.

According to another aspect of the invention, there is provided a pharmaceutical composition comprising a pharmaceutically effective amount of a compound of the first aspect of the invention.

Preferably the pharmaceutical composition comprises a compound chosen from the preferred compounds of the first aspect of the invention; more preferably the compound is chosen from the more preferred compounds of the first aspect. Most preferably the compound is the compound of formula Ib or Ic.

In another aspect the invention provides methods for treatment of diseases or conditions in which it is desirable to decrease the level of T lymphocyte activity. The methods comprise administering a pharmaceutically effective dose of a compound of the invention to a patient requiring treatment.

The diseases include T-cell malignancies and autoimmune diseases including arthritis and lupus. This aspect of the invention also includes use of the compounds for immunosuppression for organ transplantation and for inflammatory disorders. The invention includes use of the compounds for manufacture of medicaments for these treatments.

In another aspect the invention provides a method for treatment and/or prophylaxis of parasitic infections, particularly those caused by protozoan parasites. Included among the protozoan parasites are those of the genera Giardia, Trichomonas, Leishmania, Trypanosoma, Crithidia, Herpetomonas, Leptomonas, Histomonas, Eimeria, Isopora and Plasmodium. An example of a parasitic infection caused by Plasmoodium is malaria. The method can be advantageously applied with any parasite containing one or more nucleoside hydrolases inhibited by the compound of the invention when administered in an amount providing an effective concentration of the compound at the location of the enzyme.

In another aspect, the invention provides a method of preparing the compounds of the first aspect of the invention. The method may include one or more of methods (A)–(Z) and (AA)–(AF).

Method (A): (4-hydroxypyrrolo[3,2-d]pyrimidines and access to 5'-deoxy-, 5'-deoxy-5'-halogeno-, 5'-ether and 5'-thio-analogues)

reacting a compound of formula (II)

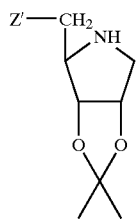

(II)

[wherein Z' is a hydrogen or halogen atom, a group of formula SQ or OQ, or a trialkylsilyloxy, alkyldiarylsilyloxy or optionally substituted triarylmethoxy group and Q is an optionally substituted alkyl, aralkyl or aryl group,] (typically Z' is a tert-butyldimethylsilyloxy, trityloxy or similar group) sequentially with N-chlorosuccinimide then a sterically hindered base (such as lithium tetramethylpiperadide) to form an imine, then with the anion of acetonitrile (typically made by treatment of acetonitrile with n-butyllithium) followed by di-tert-butyl dicarbonate. This generates a compound of formula (III)

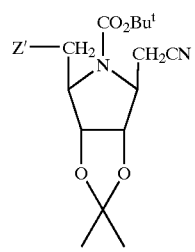

(III)

[wherein Z' is as defined for formula (II) where first shown above] which is then elaborated following the approach used to prepare 9-deazainosine [Lim et al., *J. Org. Chem.*, 48 (1983) 780] in which a compound of formula (III) is condensed with $(Me_2N)_2CHOBu^t$ and hydrolyzed under weakly acidic conditions to a compound of formula (IV)

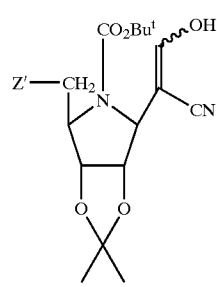

(IV)

[wherein Z' is as defined for formula (II) where first shown above] which is then sequentially condensed with a simple ester of glycine (e.g. ethyl glycinate) under mildly basic conditions, cyclized by reaction with a simple ester of chloroformic acid (e.g. benzyl chloroformate or methyl chloroformate) and then deprotected on the pyrrole nitrogen by hydrogenolysis in the presence of a noble metal catalyst (e.g. Pd/C) in the case of a benzyl group or under mildly basic conditions in the case of a simple alkyl group such as a methyl group, to give a compound of formula (V)

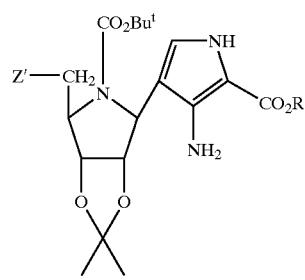

(V)

[wherein Z' is as defined for formula (II) where first shown above, and R is an alkyl group] (typically R is a methyl or ethyl group) which is then condensed with formamidine acetate to give a compound of formula (VI)

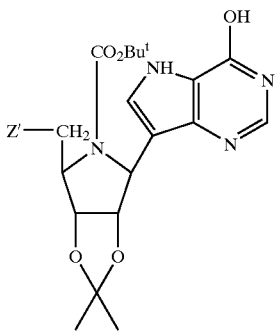

(VI)

[wherein Z' is as defined for formula (II) where first shown above] which is then fully deprotected under acidic conditions, e.g. by treatment with trifluoroacetic acid.

Methods for the preparation of a compound of formula (II) wherein Z' is a tert-butyldimethylsilyloxy group are detailed in Furneaux et al, Tetrahedron 53 (1997) 2915 and references therein.

A compound of formula (II) [wherein Z' is a halogen atom], can be prepared from a compound of formula (II) [wherein Z' is a hydroxy group], by selective N-alkyl- or aralkyl-oxycarbonylation (typically with di-tert-butyl dicarbonate, benzyl chloroformate, or methyl chloroformate and a base) or N-acylation (typically with trifluoroacetic anhydride and a base) to give a compound of formula (VII):

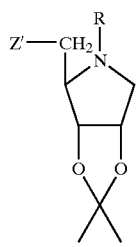

(VII)

[wherein R is an alkyl- or aralkyl-oxycarbonyl group or an optionally substituted alkyl- or aryl-carbonyl group and Z' is a hydroxy group] which is then either:

(i) 5-O-sulfonylated (typically with p-toluenesulfonyl chloride, methanesulfonyl chloride or trifluoromethanesulfonic anhydride and a base) to give a compound of formula (VII) [wherein R is an alkyl- or aralkyl-oxycarbonyl group or an optionally substituted alkyl- or aryl-carbonyl group and Z' is an optionally substituted alkyl- or aryl-sulfonyloxy group], then subjected to a sulfonate displacement reaction with a reagent capable of providing a nucleophilic source of halide ion (typically sodium, lithium or a tetraalkylammonium fluoride, chloride, bromide, or iodide); or (ii) subjected to a reagent system capable of directly replacing a primary hydroxy group with a halogen atom, for example as in the Mitsunobu reaction (e.g. using triphenylphosphine, diethyl azodicarboxylate and a nucleophilic source of halide ion as above), by reaction with diethylaminosulfur trifluoride (DAST), or by reaction with methyltriphenoxyphosphonium iodide in dimethylformamide [see e.g. Stoeckler et al, Cancer Res., 46 (1986) 1774] or by reaction with thionyl chloride or bromide in a polar solvent such as hexamethylphosphoramide [Kitagawa and Ichino, Tetrahedron Lett., (1971) 87] to give a compound of formula (VII) [wherein R is an alkyl- or aralkyl-oxycarbonyl group or an optionally substituted alkyl- or aryl-carbonyl group and Z' is a halogen atom], which is then selectively N-deprotected by acid- or alkali-catalyzed hydrolysis or alcoholysis or catalytic hydrogenolysis as required for the N-protecting group in use.

A compound of formula (VII) [wherein R is an alkyl- or aralkyl-oxycarbonyl group or an optionally substituted alkyl- or aryl-carbonyl group and Z' is a hydroxy group] can also be prepared from a compound of formula (II) [wherein Z' is a trialkylsilyloxy, alkyldiarylsilyloxy or optionally substituted triarylmethoxy group], by N-alkyl- or aralkyl-carboxylation or N-acylation as above, then selective 5-O-deprotection by acid-catalyzed hydrolysis or alcoholysis, catalytic hydrogenolysis, or treatment with a source of fluoride ion (eg tetrabutylammonium fluoride) as required for the 5-O-protecting group in use.

The compound of formula (II) [wherein Z' is a hydrogen atom] can be prepared from either:
  (i) a 5-hydroxy compound of formula (VII) [wherein R is an alkyl- or aralkyl-oxycarbonyl group or an optionally substituted alkyl- or aryl-carbonyl group and Z' is a hydroxy group], by formation and radical deoxygenation of a 5-O-thioacyl derivative; or
  (ii) a 5-deoxy-5-halogeno-compound of formula (VII) [wherein Z' is a chlorine, bromine or iodine atom] by reduction, either using a hydride reagent such as tributyltin hydride under free radical conditions, or by catalytic hydrogenolysis, typically with hydrogen over a palladium catalyst; followed by selective N-deprotection by acid- or alkali-catalyzed hydrolysis or alcoholysis or catalytic hydrogenolysis as required for the N-protecting group in use.

A compound of formula (II) [wherein Z' is an optionally substituted alkylthio, aralkylthio or arylthio group] can be prepared by reaction of a 5-deoxy-5-halogeno or a 5-O-sulfonate derivative of formula (VII) [wherein R is an alkyl- or aralkyl-oxycarbonyl group or an optionally substituted alkyl- or aryl-carbonyl group and Z' is a halogen atom or an optionally substituted alkyl- or aryl-sulfonyloxy group] mentioned above, with an alkali metal or tetraalkylammonium salt of the corresponding optionally substituted alkylthiol, aralkylthiol or arylthiol followed by selective N-deprotection by acid- or alkali-catalyzed hydrolysis or alcoholysis or catalytic hydrogenolysis as required for the N-protecting group in use [see e.g. Montgomery et al., J. Med. Chem., 17 (1974) 1197].

The compound of formula (II) (wherein Z' is a group of formula OQ, and Q is an optionally substituted alkyl, aralkyl or aryl group] can be prepared from a 5-hydroxy compound of formula (VII) [wherein R is an alkyl- or aralkyl-oxycarbonyl group or an optionally substituted alkyl- or aryl-carbonyl group and Z is a hydroxy group], by
  (i) reaction with an alkyl or aralkyl halide in the presence of a base (e.g. methyl iodide and sodium hydride, or benzyl bromide and sodium hydride, in tetrahydrofuran as solvent); or
  (ii) sequential conversion to a 5-O-sulfonate derivative (as above) and reaction with an alkali metal or tetraalkylammonium salt of the desired phenol, followed by selective N-deprotection by acid- or alkali-catalyzed hydrolysis or alcoholysis or catalytic hydrogenolysis as required for the N-protecting group in use.

It will be appreciated that the conversions above are conventional reactions employed in carbohydrate chemistry. Many alternative reagents and reaction conditions can be employed that will effect these conversions, and references to many of these can be found in the Specialist Periodical Reports "Carbohydrate Chemistry", Volumes 1–28, published by the Royal Society of Chemistry, particularly in the chapters on Halogeno-sugars, Amino-sugars, Thio-sugars, Esters, Deoxy-sugars, and Nucleosides.

Method (B): (2-amino-4-hydroxypyrrolo[3,2-d] pyrimidines)

reacting a compound of formula (V) [wherein Z' is as defined for formula (II) where first shown above, and R is an alkyl group] with benzoyl isothiocyanate then methyl iodide in the presence of a base (e.g. DBU or DBN) following the approach used to prepare 9-deazaguanosine and its derivatives [see e.g. Montgomery et al., J. Med. Chem. 36 (1993) 55, Lim et al., J. Org. Chem., 48 (1983) 780, and references therein] to give a compound of formula (VIII)

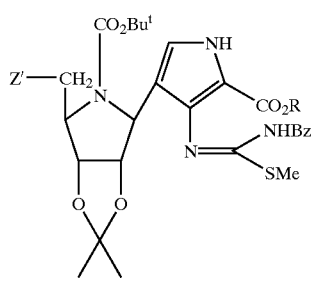

(VIII)

[wherein Z' is a trialkylsilyloxy, alkyldiarylsilyloxy or optionally substituted triarylmethoxy group, a hydrogen or halogen atom, SQ or OQ wherein Q is an optionally substituted alkyl, aralkyl or aryl group and R is an alkyl group] (typically Z', when a protected hydroxy group, is a tert-butyldimethylsilyloxy, trityloxy or similar group, and R is a methyl or ethyl group) which is then cyclized in the presence of ammonia to give a separable mixture of compounds of formula (IX)

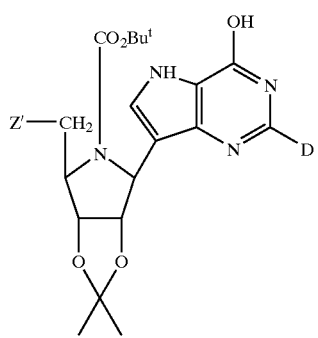

(IX)

[wherein D is an amino or methylthio group, and Z' and R are as defined for formula (VIII) where first shown above, or Z' is a hydroxy group] (where for example a tert-butyldimethylsilyloxy group has been cleaved under the reaction conditions) and the product of formula (IX) [wherein D is an amino or methylthio group] is fully deprotected under acidic conditions by the procedures set out in Method (A).

Method (C): (4-aminopyrrolo[3,2-d]pyrimidines)

reacting a compound of formula (IV) [wherein Z' is as defined for formula (II) where first shown above] with aminoacetonitrile under mildly basic conditions, cyclization of the product by reaction with a simple ester of chloroformic acid (typically benzyl chloroformate or methyl chloroformate) to give a compound of formula (X)

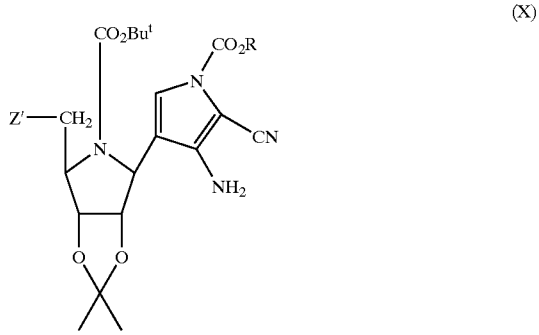

(X)

[wherein Z' is a trialkylsilyloxy, alkyldiarylsilyloxy- or optionally substituted triarylmethoxy group, a hydrogen or halogen atom, SQ or OQ wherein Q is an optionally substituted alkyl, aralkyl or aryl group and R is an aralkyl or alkyl group] (typically Z', when a protected hydroxy group, is a tert-butyldimethylsilyloxy, trityloxy or similar group, and R is a benzyl or methyl group) which is then deprotected on the pyrrole nitrogen by hydrogenolysis in the presence of a noble metal catalyst (e.g. Pd/C) in the case of a benzyl group or under mildly basic conditions in the case of a simple alkyl group such as a methyl group, and processed as described above for the transformation (V)→(VI)→(I) or (V)→(VIII)→(IX)→(I). This method follows the approach used to prepare 9-deazaadenosine and its analogues [Lim and Klein, Tetrahedron Lett., 22 (1981) 25, and Xiang et al., Nucleosides Nucleotides 15 (1996) 1821].

Method (D): (7-hydroxypyrazolo[4,3-d]pyrimidines—Daves' Methodology)

reacting a compound of formula (II) [as defined where first shown above] sequentially with N-chlorosuccinimide and a hindered base (such as lithium tetramethylpiperidide) to form an imine, then condensing this with the anion produced by abstraction of the bromine or iodine atom from a compound of formula (XIb) or (XIc)

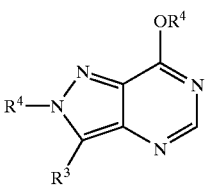

(XIa)

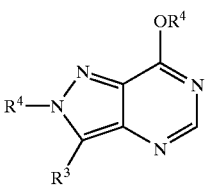

(XIb)

[wherein $R^3$ is a bromine or iodine atom and $R^4$ is a tetrahydropyran-2-yl group] typically using butyllithium or magnesium, to give a product which is then fully deprotected under acidic conditions (as in Method (A)). Methods for preparing compounds of formula (XIb) and (XIc) and mixtures thereof are described in Zhang and Daves, J. Org. Chem., 57 (1992) 4690, Stone et al., J. Org. Chem., 44 (1979) 505, and references therein.

It will be appreciated that while the tetrahydropyran-2-yl group is favoured as the protecting group for this reaction, other O,N-protecting groups can be used, and that this method will also be applicable to the synthesis of analogous pyrazolo[4,3-d]pyrimidines bearing substituents at position-5 and/or -7 of the pyrazolo[4,3-d]pyrimidine ring independently chosen from a hydroxy group, an amino, alkylamino, or aralkylamino group or a hydrogen atom using analogues of compounds of formula (XIb) and (XIc) in which the ionizable hydrogen atoms of any hydroxy or amino groups have been replaced by a suitable protecting groups.

Method (E): (7-hydroxypyrazolo[4,3-d]pyrimidines—Yokoyama Method)

subjecting a 5-O-ether protected 2,3-O-isopropylidene-D-ribofuranose derivative, where the 5-ether substituent is typically a trialkylsilyl, alkyldiarylsilyl, an optionally substituted triarylmethyl or an optionally substituted aralkyl group, particularly a tert-butyldimethylsilyl, tert-butyldiphenylsilyl, triisopropylsilyl, trityl or benzyl group, to the following reaction sequence:

(i) condensation with the anion produced by abstraction of the bromine or iodine atom from a compound of formula (XIb) or (XIc) from Method (D);

(ii) oxidation of the resulting diol to a diketone, typically using a Swern oxidation or a variant thereof using a dimethylsulfoxide-based oxidant (e.g. using a dimethylsulfoxide and trifluoroacetic anhydride reagent combination in dichloromethane solution at low temperature, typically −78° C., followed by triethylamine and warming to room temperature);

(iii) double reductive amination to form a 1,4-dideoxy-1,4-imino-D-ribitol moiety, typically with sodium cyanoborohydride and ammonium formate, ammonium acetate or benzhydrylamine in methanol; and (iv) removal of the protecting groups by acid-catalyzed hydrolysis (e.g. with 70% aqueous trifluoroacetic acid) and if required (as in the case of the product made with benzhydrylamine or where an optionally substituted aralkyl group has been used for protecting the primary hydroxyl group in the iminoribitol moiety) hydrogenolysis over a metal catalyst (typically a palladium catalyst) or if desired (as in the case of silyl ether protecting group) exposure to a reagent capable of acting as a source of fluoride ion, e.g. tetrabutylammonium fluoride in tetrahydrofuran or ammonium fluoride in methanol). Conditions suitable for effecting this sequence of reactions are reported in Yokoyama et al., J. Org. Chem., 61 (1996) 6079, and conditions for double reductive amination with ammonium acetate or benzhydrylamine can be found in Furneaux et al., Tetrahedron 42 (1993) 9605 and references therein.

Method (F): (7-hydroxypyrazolo[4,3-d]pyrimidines—the Kalvoda Method)

reacting a compound of formula (II) [as defined where first shown above] sequentially with N-chlorosuccinimide and a hindered base (such as lithium tetramethylpiperadide) to form an imine, then with a combination of trimethylsilyl cyanide and a Lewis acid (typically boron trifluoride diethyl etherate) followed by acid catalyzed hydrolysis to give a compound of formula (XII)

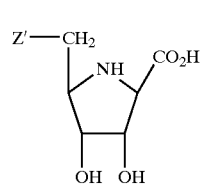

(XII)

[wherein Z' is a hydrogen or halogen atom, a hydroxy group, or a group of formula SQ or OQ where Q is an optionally substituted alkyl, aralkyl or aryl group] which is then converted by sequential selective N-protection (typically with trifluoroacetic anhydride, di-tert-butyl dicarbonate, benzyl chloroformate, or methyl chloroformate and a base), and O-protection with an acyl chloride or anhydride and a base (typically acetic anhydride or benzoyl chloride in pyridine) to a suitably protected derivative of formula (XIII)

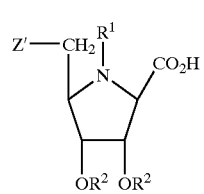

(XIII)

[wherein $R^1$ is an alkyl- or aralkyl-oxycarbonyl group or an optionally substituted alkyl- or aryl-carbonyl group, Z' is a hydrogen or a halogen atom, a group of formula SQ or OQ where Q is an optionally substituted alkyl, aralkyl or aryl group, or a group of formula $R^2O$, and $R^2$ is an alkylcarbonyl or optionally substituted arylcarbonyl group] (typically $R^1$ will be a trifluoroacetyl, tert-butoxycarbonyl or benzyloxycarbonyl group, and $R^2$ will be an acetyl or benzoyl group).

The carboxylic acid moiety in the resulting compound of formula (XIII) is then transformed into a pyrazolo[4,3-d]pyrimidin-7-one-3-yl moiety following the method described by Kalvoda [Collect. Czech. Chem. Commun., 43 (1978) 1431], by the following sequence of reactions:

(i) chlorination of the carboxylic acid moiety to form an acyl chloride, typically with thionyl chloride with a catalytic amount of dimethylformamide in an inert solvent;

(ii) use of the resulting acyl chloride to acylate hydrogen cyanide in the presence of tert-butoxycarbonyltriphenylphosphorane (i.e. $Ph_3P=CHCO_2Bu^t$) to give a 3-cyano-2-propenoate derivative;

(iii) cycloaddition of this with diazoacetonitrile (which can be prepared from aminoacetonitrile hydrochloride and sodium nitrite) with concomitant elimination of hydrogen cyanide to give a pyrazole derivative;

(iv) acid-catalyzed hydrolysis of the tert-butyl a ester in this pyrazole derivative to its equivalent carboxylic acid;

(v) Curtius reaction, typically with phenylphosphoryl azide and 2,2,2-trichloroethanol in the presence of triethylamine, which converts the carboxylic acid moiety into a 2,2,2-trichloroethoxycarbonylamino group (i.e. the product is a carbamate);

(vi) reductive cleavage of this trichloroethyl carbamate, typically with zinc dust in methanol containing ammonium chloride;

(vii) condensation of the resulting ethyl 4-amino-3-substituted-1H-pyrazole-5-carboxylate with formamidine acetate to give a compound of formula (XIV)

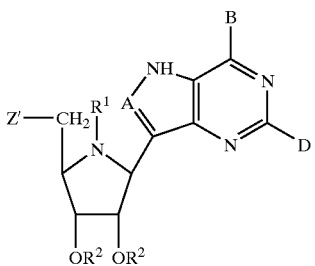

(XIV)

[wherein R¹ is an alkyl- or aralkyl-oxycarbonyl group or an optionally substituted alkyl- or aryl-carbonyl group, Z' is a hydrogen or a halogen atom, SQ or OQ where Q is an optionally substituted alkyl, aralkyl or aryl group, or a group of formula R²O, and R² is an alkylcarbonyl or optionally substituted arylcarbonyl group, A is a nitrogen atom, B is a hydroxy group and D is a hydrogen atom] which is then—and O-deprotected by acid- or alkali-catalyzed hydrolysis or alcoholysis or catalytic hydrogenolysis as required for the O- and N-protecting groups in use.

Method (G): (7-aminopyrazolo[4,3-d]pyrimidines—the Buchanan Method)

reacting a compound of formula (II) [as defined where first shown above] sequentially with N-chlorosuccinimide and a hindered base (such as lithium tetramethylpiperadide) to form an imine, which is then transformed into a 7-aminopyrazolo[4,3-d]pyrimidine derivative following the approach used to prepare formycin and its analogues by Buchanan and co-workers [J. Chem. Soc., Perkin Trans. I (1991) 1077 and references therein], by the following sequence of reactions:

(i) addition of 3,3-diethoxyprop-1-ynylmagnesium bromide or 3,3-diethoxyprop-1-ynyllithium to the imine;

(ii) N-protection, typically with trifluoroacetic anhydride, di-tert-butyl dicarbonate, benzyl chloroformate, or methyl chloroformate and a base;

(iii) mild acid hydrolysis to remove the acid sensitive O-protecting groups and convert the diethyl acetal moiety into an aldehydic moiety;

(iv) condensation with hydrazine to convert the 3-substituted prop-2-ynal derivative into a 3-substituted pyrazole derivative;

(v) acylation, typically with acetic anhydride or benzoyl chloride in pyridine;

(vi) nitration, typically with ammonium nitrate, trifluoroacetic anhydride and trifluoroacetic acid, to produce an 3-substituted 1,4-dinitopyrazole derivative;

(vii) reaction with a reagent capable of delivering cyanide ion, typically sodium cyanide in aqueous ethanol to cause a cine-substitution of one of the two nitro-groups;

(viii) reduction of the residual nitro-group, typically with sodium dithionite or by catalytic hydrogenation over a metal catalyst;

(ix) condensation with formamidine acetate to give a compound of formula (XIV) [wherein R¹ is an alkyl- or aralkyl-oxycarbonyl group or an optionally substituted alkyl- or aryl-carbonyl group, Z' is a hydrogen or a halogen atom, SQ or OQ where Q is an optionally substituted alkyl, aralkyl or aryl group, or a group of formula R²O wherein R² is an alkylcarbonyl or optionally substituted arylcarbonyl group, A is a nitrogen atom, B is an amino group and D is a hydrogen atom] which is then—and O-deprotected by acid- or alkali-catalyzed hydrolysis or alcoholysis or catalytic hydrogenolysis as required for the O- and N-protecting groups in use.

Method (H): (2'-deoxy-analogues)

effecting the overall 2'-deoxygenation of a compound of formula (I) [wherein X and Z are hydroxy groups, Y is a hydrogen atom, and A, B and D are as defined where this formula is first shown above] through sequential:

(i) selective N-alkyl- or aralkyl-oxycarbonylation (typically with di-tert-butyl dicarbonate, benzyl chloroformate, or methyl chloroformate and a base) or N-acylation (typically with trifluoroacetic anhydride and a base) of the 1,4-dideoxy-1,4-iminoribitol moiety in such a compound of formula (I); and (ii) 3',5'-O-protection of the resulting product by reaction with 1,3-dichloro-1,1,3,3-tetraisopropyldisiloxane and a base to give a compound of formula (XV):

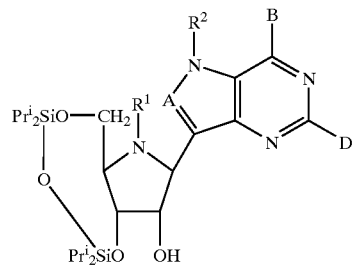

(XV)

[wherein R¹ is an alkyl- or aralkyl-oxycarbonyl group or an optionally substituted alkyl- or aryl-carbonyl group, R² is either the same as R¹ or is a hydrogen atom, and A, B and D are as defined for formula (I) where first shown above]

(iii) 2'-O-thioacylation of the resulting compound of formula (XV) (typically with phenoxythionocarbonyl chloride and a base; or sodium hydride, carbon disulfide and methyl iodide);

(iv) Barton radical deoxygenation (typically with tributyltin hydride and a radical initiator);

(v) cleavage of the silyl protecting group by a reagent capable of acting as a source of fluoride ion, e.g. tetrabutylammonium fluoride in tetrahydrofuran or ammonium fluoride in methanol; and (vi) cleavage of the residual N- and O-protecting groups by acid- or alkali-catalyzed hydrolysis or alcoholysis or catalytic hydrogenolysis as required for the protecting groups in use.

Reagents and reaction conditions suitable for conducting the key steps in this transformation can be found in Robins et al., J. Am. Chem. Soc., 105 (1983) 4059; Solan and Rosowsky, Nucleosides Nucleotides 8 (1989) 1369; and Upadhya et al., Nucleic Acid Res., 14(1986) 1747.

It will be appreciated that a compound of formula (I) has a nitrogen atom in its pyrrole or pyrazole ring capable of undergoing alkyl- or aralkyl-oxycarbonylation or acylation during step (i), or thioacylation during step (ii), depending upon the reaction conditions employed. Should such derivatives be formed, the pyrrole or pyrazole N-substituents in the resulting derivatives are either sufficiently labile that they can be removed by mild acid- or alkali-catalyzed hydrolysis or alcoholysis, or do not interfere with the subsequent chemistry in the imino-ribitol moiety, and can be removed during the final deprotection step(s). If desired, this approach can be applied to a compound of formula (XV) [as defined above, but additionally bearing N-protecting groups on the. pyrazolo- or pyrrolo-pyrimidine moiety]. Methods suitable for preparing such N-protected compounds can be found in Ciszewski et al., Nucleosides Nucleotides 12 (1993) 487; and Kambhampati et al., Nucleosides and Nucleotides 5 (1986) 539, as can methods to effect their 2'-deoxygenation, and conditions suitable for N-deprotection.

Method (I): (2'-epi-analoques)

effecting the overall C-2' epimerization of a compound of formula (I), by oxidizing and then reducing a compound of formula (XV) [as defined where first shown above] to give compound of formula (XVI):

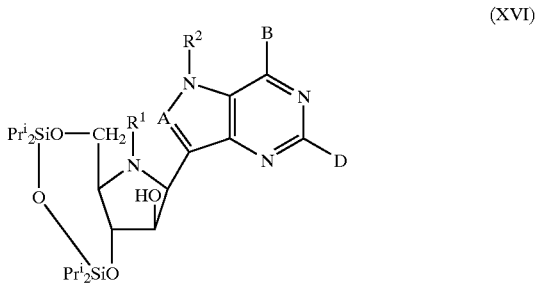

(XVI)

[wherein $R^1$, $R^2$, A, B and D are as defined for formula (XV) where first shown above] which may be present in a mixture with the starting alcohol of formula (XV), and then fully deprotecting this compound of formula (XVI) as set out in steps (v) and (vi) of Method (H).

Reagents and reaction conditions suitable for conducting the key steps in this transformation can be found in Robins et al., Tetrahedron 53 (1997) 447.

Method (J): (2'-deoxy-2'-halogeno- and 2'-deoxy-2'-epi-2'-halogeno-analogues)

reacting compound of formula (XV) or (XVI) [as defined where first shown above] by the methods set out in Method (A) for the preparation of a compound of formula (II) [wherein Z' is a halogen atom] which involve either:

(i) 2'-O-sulfonylation and sulfonate displacement with a halide ion; or (ii) direct replacement of the 2'-hydroxy group with a halogen atom, e.g by the Mitsunobu reaction or reaction with diethylaminosulfur trifluoride (DAST) to give a compound of inverted stereochemistry at C-2', which is then fully deprotected as set out in steps (v) and (vi) of Method (H).

It will be appreciated that a compound of formula (XV) or (XVI) has a nitrogen atom in its pyrrole or pyrazole ring capable of undergoing sulfonylation during step (i), depending upon the reaction conditions employed. Should such derivatives be formed, the pyrrole or pyrazole N-sulfonate substituents in the resulting derivatives are either sufficiently labile that they can be removed by mild acid- or alkali-catalyzed hydrolysis or alcoholysis, or do not interfere with the subsequent chemistry in the iminoribitol moiety, and can be removed during the final deprotection step(s).

If desired, this approach can be applied to a compound of formula (XV) or (XVI) [as defined above, but additionally bearing N-protecting groups on the pyrazolo- or pyrrolo-pyrimidine moiety]. Methods suitable for preparing such N-protected compounds can be found in Ciszewski et al., Nucleosides Nucleotides 12 (1993) 487; and Kambhampati et al., Nucleosides and Nucleotides 5 (1986) 539, as can methods to effect 2'-O-triflate formation and displacement by halide ion with inversion, and conditions suitable for N-deprotection.

Method (K): (5'-deoxy-, 5'-deoxy-5'-halogeno-, 5'-ether and 5'-thio-analogues)

by applying the procedures described in Method (A) for converting a compound of formula (VII) [wherein R is an alkyl- or aralkyl-oxycarbonyl group or an optionally substituted alkyl- or aryl-carbonyl group and Z' is a hydroxy group] into a compound of formula (II) [wherein Z' is a halogen or hydrogen atom or SQ or OQ where Q is an optionally substituted alkyl, aralkyl or aryl group alkylthio group of one to five carbon atoms] to a compound of formula (XVII):

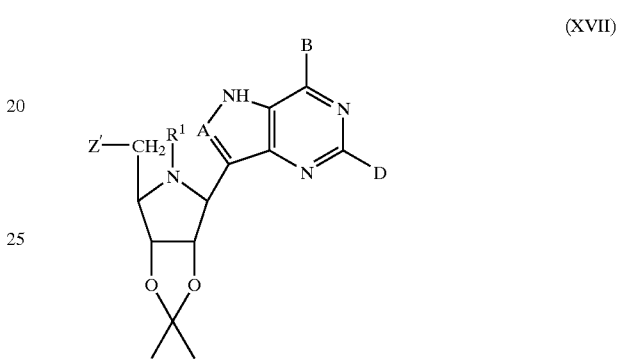

(XVII)

[wherein R is an alkyl- or aralkyl-oxycarbonyl group or an optionally substituted alkyl- or aryl-carbonyl group, Z' is a hydroxy group, and A, B and D are as defined for formula (I) where first shown above] which is then fully deprotected under acidic conditions, e.g. by treatment with aqueous trifluoroacetic acid.

Such a compound of formula (XVII) can be prepared from a compound of formula (I) [wherein X and Z are both hydroxy groups, Y is a hydrogen atom and A, B, and D have the meanings defined for formula (I) where first shown above] in the following two reaction steps, which may be applied in either order:

(i) selective N-alkyl- or aralkyl-oxycarbonylation (typically with di-tert-butyl dicarbonate, benzyl chloroformate, or methyl chloroformate and a base) or N-acylation (typically with trifluoroacetic anhydride and a base) of the 1,4-dideoxy-1,4-iminoribitol moiety; and (ii) 2',3'-O-isopropylidenation, which may be effected with a variety of reagents, e.g. acetone and anhydrous copper sulfate with or without added sulfuric acid; acetone and sulfuric acid; 2,2-dimethoxypropane and an acid catalyst; or 2-methoxypropene and an acid catalyst.

It will be appreciated that such a compound of formula (I) or formula (XVII) has a nitrogen atom in its pyrrole or pyrazole ring capable of undergoing sulfonylation, thioacylation, acylation or aralkyl-oxycarbonylation, depending upon the reaction conditions employed. Should such derivatives be formed, the pyrrole or pyrazole N-substituents in the resulting derivatives are either sufficiently labile that they can be removed by mild acid- or alkali-catalyzed hydrolysis or alcoholysis, or do not interfere with the subsequent chemistry in the iminoribitol moiety, and can be removed during the final deprotection step(s).

Method (L): (2- and 4-aminopyrrolo[3,2-d]pyrimidine and 5-and 7-aminopyrazolo[4,3-d]pyrimidine analogues) chlorinating a compound of formula (XVIII)

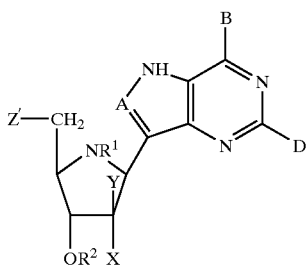

[wherein $R^1$ is an alkyl- or aralkyl-oxycarbonyl group or an optionally substituted alkyl- or aryl-carbonyl group, $R^2$ is an alkylcarbonyl or optionally substituted arylcarbonyl group, X and Y are independently chosen from a hydrogen or halogen atom, or a group of formula $R^2O$, except that when one of X or Y is a halogen atom or a group of formula $R^2O$, the other is a hydrogen atom, Z' is a group of formula $R^2O$ or, when X is a group of formula $R^2O$, Z' is a hydrogen or halogen atom, a group of formula $R^2O$ or of formula OQ or SQ wherein Q is an optionally substituted alkyl, aralkyl or an aryl group, A is a nitrogen atom or a methane group, and one of B or D is a hydroxy group, and the other is a chlorine, bromine or hydrogen atom] with a chlorinating reagent, and then displacing the chlorine atom with a nitrogen nucleophile by one of the following methods:

(i) ammoniolysis, typically using liquid ammonia, concentrated aqueous ammonia, or a solution of ammonia in an alcohol such as methanol; or (ii) conversion first to a triazole derivative, by addition of 4-chlorophenyl phosphorodichloridate to a solution of the chloride and 1,2,4-triazole in pyridine, and alkaline hydrolysis of both the tetrazole moiety and the ester protecting groups with ammonium hydroxide;

(iii) reaction with a source of azide ion, e.g. an alkali metal azide or tetraalkylammonium azide, and reduction of the resulting product, typically by catalytic hydrogenation; or (iv) reaction with an alkylamine or aralkylamine, such as methylamine or benzylamine in methanol.

These conditions are sufficiently basic that O-ester groups will generally be cleaved but any residual O- or N-protecting groups can then be removed by acid- or alkali-catalyzed hydrolysis or alcoholysis or catalytic hydrogenolysis as required for the protecting groups in use.

Suitable chlorinating agents are thionyl chloride—dimethylformamide complex [Ikehara and Uno, Chem. Pharm. Bull., 13 (1965) 221], triphenylphosphine in carbon tetrachloride and dichloromethane with or without added 1,8-diazabicyclo[5.4.0]undec-7-ene (DBU) [De Napoli et al., J. Chem. Soc., Perkin Trans.1 (1995) 15 and references therein], phosphoryl chloride [Imai, Chem. Pharm. Bull., 12 (1964) 1030], or phenylphosphoryl chloride and sodium hydride.

Suitable conditions for such an ammoniolysis or a reaction with an alkylamine can be found in Ikehara and Uno, Chem. Pharm. Bull., 13 (1965) 221; Robins and Tripp, Biochemistry 12 (1973) 2179; Marumoto et al., Chem. Pharm. Bull., 23 (1975) 759; and Hutchinson et al., J. Med. Chem., 33 (1990) 1919].

Suitable conditions for conversion of a such a chloride to an amine via a tetrazole derivative can be found in Lin et al., Tetrahedron 51 (1995) 1055.

Suitable conditions for reaction with azide ion followed by reduction can be found in Marumoto et al., Chem. Pharm. Bull., 23 (1975) 759.

Such a compound of formula (XVIII) can be prepared from a compound of formula (I) by selective N-alkyl- or aralkyl-oxycarbonylation (typically with di-tert-butyl dicarbonate, benzyl chloroformate, or methyl chloroformate and a base) or N-acylation of the 1,4-dideoxy-1,4-iminoribitol moiety and then O-acylation (typically with acetic anhydride or benzoyl chloride in pyridine). It will be appreciated that such a compound of formula (I) has a nitrogen atom in its pyrrole or pyrazole ring capable of undergoing alkyl- or aralkyl-oxycarbonylation or acylation depending upon the reaction conditions employed. Should such derivatives be formed, the pyrrole or pyrazole N-substituents in the resulting derivatives are either sufficiently labile that they can be removed by mild acid- or alkali-catalyzed hydrolysis or alcoholysis, or do not interfere with the subsequent chemistry, and can be removed during the final deprotection step(s).

The above chlorination—amination—deprotection sequence can also be applied to a compound of formula (XVI:) [wherein B is a hydroxy group, D is a hydrogen atom, Z' is a hydrogen or halogen atom, or a group of formula $R^2O$, $R^2$ is a trialkylsilyloxy or alkyldibrylsilyloxy group, or an optionally substituted triarylmethoxy, alkylcarbonyl or arylcarbonyl group, R and A are as defined for formula (XVII) where first shown above]. Suitable conditions for conducting this reaction sequence can be found in Ikehara et al., Chem. Pharm. Bull., 12 (1964) 267.

Method (M): (2,4-dihydroxypyrrolo [3,2-d]pyrimidine and 5,7-dihydroxypyrazolo[4,3-d]pyrimidine analogues) oxidation of either:

(i) a compound of formula (XVIII) [wherein $R^2$ is a hydrogen atom; X and Y are independently chosen from a hydrogen or halogen atom, or a hydroxy group, except that when one of X or Y is a halogen atom or a hydroxy group, the other is a hydrogen atom; Z' is a hydroxy group or, when X is a hydroxy group, Z' is a hydrogen or halogen atom, a hydroxy group, or OQ; Q is an optionally substituted alkyl, aralkyl or aryl group; B is a hydroxy group or an amino group; D is a hydrogen atom; and $R^1$ and A are as defined for formula (XVIII) where first shown above] with bromine in water; or (ii) a compound of formula (XVIII) [wherein Z' is a hydrogen or a halogen atom, or a group of formula $R^2O$, or OQ; Q is an optionally substituted alkyl, aralkyl or aryl group; B is a hydroxy group or an amino group, D is a hydrogen atom and $R^1$, $R^2$, X, Y and A are as defined for formula (XVIII) where first shown above], with bromine or potassium permanganate in water or in an aqueous solvent mixture containing an inert, water-miscible solvent to improve the solubility of the substrate, to give a related compound of formula (XVIII) [but wherein B and D are now hydroxy groups], and then removal of any O- and N-protecting groups by acid- or alkali-catalyzed hydrolysis or alcoholysis or catalytic hydrogenolysis as required for the protecting groups in use.

Such a compound of formula (XVIII) required for step (i) above can be prepared from a compound of formula (I) [wherein Z is Z', and X, Y, Z, A, B and D are as defined for the required compound of formula (XVIII)] by selective N-alkyl- or aralkyl-oxycarbonylation (typically with di-tert-butyl dicarbonate, benzyl chloroformate, or methyl chloroformate and a base) or N-acylation (typically with trifluoroacetic anhydride and a base) of the 1,4-dideoxy-1,4-iminoribitol moiety. This can then be converted to the corresponding compound of formula (XVIII) required for step (ii) above by O-acylation (typically with acetic anhydride or benzoyl chloride in pyridine). It will be appreciated that such a compound of formula (I) has a nitrogen atom in its pyrrole or pyrazole ring capable of undergoing alkyl- or aralkyl-oxycarbonylation or acylation depending upon the reaction conditions employed. Should such derivatives be formed, the pyrrole or pyrazole N-substituents in the resulting derivatives are either sufficiently labile that they can be removed by mild acid- or alkali-catalyzed hydrolysis or alcoholysis, or do not interfere with the subsequent chemistry, and can be removed during the final deprotection step(s).

Method (N): (4-amino-2-chloropyrrolo[3,2-d]pyrimidine and 7-amino-5-chloropyrazolo[4,3-d]pyrimidine analogues)

chlorinating a compound of formula (XVIII) [wherein B and D are hydroxy groups and $R^1$, $R^2$, X, Y, Z' and A are as defined for formula (XVIII) where first shown above] to give a corresponding dichloro-derivative of formula (XVIII) [wherein B and D are chlorine atoms], typically with neat phosphorous oxychloride, and then displacing the more reactive chloro-substituent selectively by ammoniolysis, typically using anhydrous liquid ammonia in a pressure bomb or methanolic ammonia, which simultaneously cleaves the O-ester protecting groups. The residual N-protecting group is then removed by acid-catalyzed hydrolysis or alcoholysis or catalytic hydrogenolysis as required for the protecting groups in use, to give a compound of formula (I) [wherein B is an amino-group and D is a chlorine atom].

The above dichloro-derivative of formula (XVIII) can be converted into a compound of formula (I) [wherein B and D are chlorine atoms] by removal of the O- and N-protecting groups by acid- or alkali-catalyzed hydrolysis or alcoholysis as required for the protecting groups in use. It will be appreciated that one of the chlorine atoms in the aforementioned compound of formula (XVIII) or of formula (I) is quite reactive and that conditions chosen for deprotection must be mild enough that they limit unwanted reactions involving this atom.

Suitable reaction conditions for the key steps in this method can be found in Upadhya et al., Nucleic Acid Res., 14 (1986) 1747 and Kitagawa et al., J. Med. Chem., 16 (1973) 1381.

Method (O): (2-chloro-4-hydroxypyrrolo[3,2-d]pyrimidine and 5-chloro-7-hydroxypyrazolo[4,3-d]pyrimidine analogues from dichloro-compounds)

hydrolysis of a compound of formula (XVIII) [wherein B and D are chlorine atoms] available as an intermediate from the first reaction of Method (N), typically with aqueous potassium hydroxide or sodium carbonate, in the presence of an inert, water-miscible solvent such as dioxane to enhance solubility as required, followed by removal of the residual N-protecting group by acid-catalyzed hydrolysis or alcoholysis or catalytic hydrogenolysis as required for the protecting groups in use, to give a compound of formula (I) [wherein B is a hydroxy group and D is a chlorine atom].

Method (P): (2-chloro-4-hydroxypyrrolo[3,2-d]pyrimidine and 5-chloro-7-hydroxypyrazolo[4,3-d]pyrimidine analogues from aminochloro-compounds)

deamination of a compound of formula (XVIII) [wherein B is an amino group, D is a chlorine atom, $R^1$ is an alkyl- or aralkyl-oxycarbonyl group or an optionally substituted alkyl- or aryl-carbonyl group, $R^2$ is a hydrogen atom, Z'=Z and X, Y, Z and A are as defined for formula (I) where first shown above), available as an intermediate following the chlorination and ammonyolysis reactions of Method (N), by reaction with nitrosyl chloride, followed by removal of the protecting groups as set out in Method (N). Typical reaction conditions can be found in Sanghvi et al., Nucleosides Nucleotides 10 (1991) 1417.

Method (Q): (4-halogenopyrrolo[3,2-d]pyrimidine and 7-halogenopyrazolo[4,3-d]pyrimidine analogues)

reacting a compound of formula (XVIII) (wherein $R^1$ is tert-butoxycarbonyl group, B is a hydroxy group, D is a hydrogen atom and $R^2$, X, Y, Z' and A are as defined for formula (XVIII) where first shown above] by a method used to prepare halogeno-formycin analogues [Watanabe et al., J. Antibiotic, Ser. A 19 (1966) 93] which involves sequential treatment with:

(i) phosphorous pentasulfide by heating in pyridine and water under reflux to give a mercapto-derivative;

(ii) methyl iodide to give a methylthio-derivative;

(iii) a base in a simple alcohol or an aqueous solution of a simple alcohol, e.g. sodium methoxide in methanol, to remove the O-protecting groups; and (iv) chlorine, bromine or iodine in absolute methanol to give a halogeno-derivative which is then N-deprotected by reaction with aqueous acid, typically a concentrated trifluoroacetic acid solution.

Method (R): (pyrrolo[3,2-d]pyrimidine and pyrazolo[4,3-d]pyrimidine analogues)

hydrogenolytic cleavage of the chloride intermediate resulting from the chlorination reaction used as the first reaction in Method (L), or the chloride intermediate resulting from the chlorination reaction step (iv) in Method (Q), or the compound of formula (I) produced by Method (Q), typically using hydrogen over palladium on charcoal as the catalyst, optionally with magnesium oxide present to neutralize released acid, followed by cleavage of any residual O- or N-protecting groups by acid- or alkali-catalyzed hydrolysis or alcoholysis as required for the protecting groups in use.

Method (S): (N-alkylated 4-aminopyrrolo[3,2-d]pyrimidine and 7-aminopyrazolo[4,3-d]pyrimidine analogues)

heating an O-deprotected methylthio-derivative produced by step (iii) of Method (Q) with an amine, e.g. methylamine, in absolute methanol in a sealed tube or bomb, and then removing the N-protecting group by reaction with aqueous acid, typically a concentrated trifluoroacetic acid solution. This method has been used to prepare N-alkylated-formycin analogues [Watanabe et al., J. Antibiotic, Ser. A 19 (1966) 93]; or reacting a compound of formula (I) [wherein either B or D is an amino group] with 1,2-bis[(dimethylamino)methylene]hydrazine and trimethylsilyl chloride in toluene to convert the amino group into a 1,3,4-triazole group, hydrolysis to cleave the O-silyl groups (e.g. with acetic acid in aqueous acetonitrile), and displacement of the 1,3,4-triazole group with an alkylamine in a polar solvent (e.g. water or aqueous pyridine). This method has been used to prepare N,N-dimethyl-formycin A [Miles et al., J. Am. Chem. Soc., 117 (1995) 5951]; or subjecting a compound of formula (I) [wherein either B or D is an amino group] to an exchange reaction by heating it with an excess of an alkylamine. This method has been used to prepare N-alkyl-formycin A derivatives [Hecht et al., J. Biol. Chem., 250 (1975) 7343].

Method T: (2-chloro-4-hydroxypyrrolo[3,2-d]pyrimidine and 5-chloro-7-hydroxypyrazolo[4,3-d]pyrimidine analogues)

Selective chlorination of dihydroxy compound of formula (XVIII) [wherein B and D are hydroxy groups, and $R^1$, $R^2$, X, Y, Z' and A are as defined for formula (XVIII) where first shown above], taking advantage of the greater reactivity of the 4-hydroxy group on a 2,4-dihydroxypyrrolo[3,2-d] pyrimidine derivative and the 7-hydroxy group on a 5,7-dihydroxypyrazolo[4,3-d]pyrimidine derivative, followed by removal of protecting groups, using the methods set out in Method (N).

Method U: (2-halogeno-, 4-halogeno- and 2,4-dihalogeno-pyrrolo[3,2-d]pyrimidine and 5-halogeno-, 7-halogeno-, and 5,7-dihalogeno-pyrazolo[4,3-d]pyrimidine analogues) diazotization of a compound of formula (XVIII) [wherein one of B or D is an amino group, and the other is independently chosen from an amino group, or a halogeno or hydrogen atom, and $R^1$, $R^2$, X, Y, Z' and A are as defined for formula (XVIII) where first shown above] and subsequent reaction using one of the following procedures:

(i) with nitrous acid (made in situ from sodium nitrite) in the presence of a source of halide ion. For replacement of an amino-group with a fluorine atom, a concentrated aqueous solution of fluoroboric acid [Gerster and Robins, J. Org. Chem., 31 (1966) 3258; Montgomery and Hewson, J. Org. Chem., 33 (1968) 432] or hydrogen fluoride and pyridine at low temperature (e.g. −25 to −30° C.) [Secrist et al., J. Med. Chem., 29 (1986) 2069] can serve both as the mineral acid and the fluoride ion source; or (ii) with an alkyl nitrite, typically tert-butyl or n-butyl nitrite, in a non-aqueous solvent in the presence of a source of halide ion. For replacement of an amino-group with a chlorine atom, a combination of chlorine and cuprous chloride, or antimony trichloride can be used in chloroform as solvent [Niiya et al, J. Med. Chem., 35 (1992) 4557 and references therein]; or (iii) with an alkyl nitrite, typically tert-butyl or n-butyl nitrite, in a non-aqueous solvent coupled with photo-halogenation. For replacement of an amino group with a chlorine, bromine or iodine atom, carbon tetrachloride, bromoform, or diiodomethane have been used as reagent and solvent and an incandescent light source (e.g. a 200 W bulb) has been used to effect photohalogenation [Ford et al., J. Med. Chem., 38 (1995) 1189; Driscoll et al., J. Med. Chem., 39 (1996) 1619; and references therein]; to give a corresponding compound of formula (XVIII) [wherein B is a halogen atom and B is either a halogen atom or an amino group], followed by removal of the protecting groups as set out in Method (N).

The same transformations can be effected for a corresponding starting compound of formula (XVIII) [wherein one of B or D is an amino group, and the other is a hydroxy group] if the hydroxy group is first converted to a thiol group [Gerster and Robins, J. Org. Chem., 31 (1966) 3258]. This conversion can be effected by reaction with phosphorous pentasulfide by heating in pyridine and water under reflux (see Method (Q)).

Method (V): (4-iodo-pyrazolo[3,2-d]pyrimidine and 7-iodopyrazolo[4,3-d]pyrimidine analogues)
treatment of corresponding chloro-analogue of formula (I) [wherein B is a chlorine atom] with concentrated aqueous hydroiodic acid, following the method of Gerster et al., J. Org. Chem., 28 (1963) 945.

Method (W): (5'-deoxy-5'-halogeno- and 5'-thio-analogues)
by reacting a compound of formula (XVIII) [wherein $R^2$ is a hydrogen atom; X and Y are independently chosen from a hydrogen or halogen atom, or a hydroxy group, except that when one of X or Y is a halogen atom or a hydroxy group, the other is a hydrogen atom; Z is a hydroxy group; and $R^1$, A, B and D are as defined for formula (XVIII) where first shown above] with either (i) a trisubstituted phosphine and a disulfide, e.g. tributylphosphine and diphenyl disulfide; or
(ii) a trisubstituted phosphine (e.g. triphenylphosphine) and carbon tetrabromide; or
(iii) thionyl chloride or bromide.

and then removal of the N-protecting group by acid- or alkali-catalyzed hydrolysis or alcoholysis or catalytic hydrogenolysis as required for the protecting group in use.

Conditions suitable for conducting such selective replacements of a 5'-hydroxy group with a thio group or a halogen atom can be found in Chern et al., J. Med. Chem., 36 (1993) 1024; and Chu et al., Nucleoside Nucleotides 5 (1986) 185.

Method (X): (5'-phospho-pyrazolo[3,2-d]pyrimidine and 5'-phospho-pyrazolo[4,3-d]pyrimidine analogues)
reacting a compound of formula (XVII) [wherein R, Z', A, B and D are as defined where first shown) with (i) a phosphitylation agent, such as N,N-diethyl-1,5-dihydro-2,4,3-benzodioxaphosphepin-3-amine, then oxidizing the phosphite ester to a phosphate ester, e.g. with 3-chloroperbenzoic acid; or
(ii) a phosphorylatiing agent, such as phosphoryl chloride or dibenzylchlorophosphate; and removing the protecting groups, e.g. by hydrogenolysis and treatment under acidic conditions as set out in Method (A).

Method (Y): (3-aminopyrrole-2-carboxylic acid and 4-amino-1H-pyrazole-5-carboxylic acid analogues)
fully deprotecting a compound of formula (V) as defined where first shown, or an intermediate ethyl 4-amino-3-substituted-1H-pyrazole-5-carboxylate produced by step (vi) in Method (F), by acid- or alkali-catalyzed hydrolysis or alcoholysis or catalytic hydrogenolysis as required for the O- and N-protecting groups in use.

Method (Z): (3-amino-2-cyanopyrroles and 4-amino-5-cyano-1H-pyrazoles)
fully deprotecting a compound of formula (X) as defined where first shown above, or a 4-amino-5-cyanopyrazole intermediate produced by step (viii) in Method (G), by acid-or alkali-catalyzed hydrolysis or alcoholysis or catalytic hydrogenolysis as required for the O- and N-protecting groups in use.

Method (AA): (3-aminopyrrole-2-carboxamide and 4-amino-1H-pyrazole-5-carboxamide analogues)
conversion of the cyano-group of a compound of formula (X) as defined where first shown above, or a 4-amino-5-cyano-1H-pyrazoles intermediate produced by step (viii) in Method (G), into a carboxamido-group, conveniently by reaction with hydrogen peroxide and potassium carbonate in dimethylsulfoxide, and then fully deprotecting the resulting product by acid- or alkali-catalyzed hydrolysis or alcoholysis or catalytic hydrogenolysis as required for the O- and N-protecting group in use.

Method (AB): (3-(thio)carbamoylpyrroles and 4-(thio)carbamoyl-1H-pyrazoles)
reaction of a compound of formula (V) or formula (X) as defined where first shown above, or a protected carboxamido-intermediate as prepared in Method (AA), or an intermediate ethyl 4-amino-3-substituted-1H-pyrazole-5-carboxylate produced by step (vi) in Method (F), with an isocyanate or isothiocyanate of formula RNCO or RNCS, where R is as defined for compounds of formula (I) and then fully deprotecting the resulting product by acid- or alkali-catalyzed hydrolysis or alcoholysis or catalytic hydrogenolysis as required for the O- and N-protecting groups in use.

Method (AC): (esters of 3-aminopyrrole-2-carboxylic acid and 4-amino-1H-pyrazole-5-carboxylic acid analogues)

converting the carboxylic acid group of a compound of formula (Ia) wherein E is $CO_2H$ into an ester, which can be accomplished by a number of well known methods for esterification. Conveniently an ester can be made by reaction of the carboxylic acid in acidic solution of the alcohol, e.g., ethanolic hydrogen chloride.

Method (AD): (3-acylaminopyrroles and 4-acylamino-1H-pyrazoles)

reaction of a compound of formula (V) or (X) as defined where first shown above, or an intermediate ethyl 4-amino-3-substituted-1H-pyrazole-5-carboxylate produced by step (vi) in Method (F), with an acylating agent, e.g. an acyl chloride such as benzoyl chloride, acid anhydride such as acetic anhydride in the presence of a base, such as triethylamine, potassium carbonate or pyridine, and then fully deprotecting the resulting product acid- or alkali-catalyzed hydrolysis or alcoholysis or catalytic hydrogenolysis as required for the O- and N-protecting groups in use.

Method (AE): (N-mono- and N,N-di-substituted 3-amino-pyrrole-2-carboxamide and 4-amino-1H-pyrazole-5-carboxamide analogues)

converting the carboxylic acid group of a compound of formula (Ia) wherein E is $CO_2H$ into an amide. Conveniently an amide can be made by carbodiimide induced condensation (e.g. with N,N-dicylcohexylcarbodiimide) of the carboxylic acid with a primary or secondary amine.

Method (AF): (N-mono- and N,N-di-substituted 3-amino-pyrrole-2-carboxamide and 4-amino-1H-pyrazole-5-carboxamide analogues)

condensing a compound of formula (V) as defined where first shown, or an intermediate ethyl 4-amino-3-substituted-1H-pyrazole-5-carboxylate produced by step (vi) in Method (F), with a primary or secondary amine and fully deprotecting the resulting product by acid- or alkali-catalyzed hydrolysis or alcoholysis or catalytic hydrogenolysis as required for the O- and N-protecting groups in use.

It will be appreciated that the approaches outlined in Methods (H), (I), (J), (K) and (W) are equally applicable to the synthesis of compounds of formula (Ia) to give analogous variations in the 1,4-imino-pentitol moiety.

Method (AG): (Acyloxymethyl Ester Prodrugs)

reacting a 5-phosphate ester of a compound of formula (I) or formula (Ia) with benzylchloroformate in the presence of a base, conveniently aqueous sodium bicarbonate, to form an N-benzyloxycarbonyl derivative, reacting this derivative with an acyloxymethyl halide of formula $RCO_2CH_2X$ where R is an alkyl group such as methyl, ethyl, propyl or tert-butyl and X is chloride, bromide or iodide, in the presence of a base, to form the 5-phosphate bis(acyloxymethyl) ester. Suitable conditions for the formation of the acetoxymethyl esters, using acetoxymethyl bromide and diisopropylethylamine in dimethylformamide, can be found in Kruppa et al, *Bioorg. Med. Chem. Lett.*, 7 (1997) 945.

When desired, e.g. as when the aforementioned N-benzyloxycarbonyl derivative is not sufficiently soluble in the reaction solvent, this derivative may first be converted into the corresponding stannyl intermediates, e.g. the bis (tributylstannyl) phosphate derivative by reaction with tributyltin methoxide in methanol, prior to reaction with the acyloxymethyl halide in the presence of tetrabutylammonium bromide, following the method described by Kang et al., *Nucleosides Nucleotides* 17 (1998) 1089.

It will be appreciated that the conversion of such a 5-phosphate group to the corresponding bis(acyloxymethyl) ester can be accomplished by utilizing O- and or N-protected derivatives of compounds of formula (I) or formula (Ia) if desired, so long as the protecting groups can subsequently be removed without the use of strongly acidic or strongly basic conditions. Typically this requires the use of hydrogenolysis conditions for deprotection, so that O- and N-benzyl, -benzyloxymethyl or -benzyloxycarbonyl groups are favoured.

Further Methods

Compounds of the invention may also be prepared by other methods as will be apparent to those skilled in the art.

Further Aspects

The compounds of the invention are useful both in free base form and in the form of salts. The term "pharmaceutically acceptable salts" is intended to apply to non-toxic salts derived from inorganic or organic acids including for example salts derived from the following acids -hydrochloric, sulfuric, phosphoric, acetic, lactic, fumaric, succinic, tartaric, gluconic, citric, methanesulphonic and p-toluenesulphonic acids.

The compounds of the invention are potent inhibitors of purine nucleoside phosphorylases, nucleoside hydrolases and/or phosphoribosyltransferases. For example, the $IC_{50}$ values for the compounds of formula (Ib) and formula (Ic) are less than 0.1 nM for both calf spleen PNP and human red blood cell PNP. The examples below provide further detail of the effectiveness of this inhibitor. Purine nucleoside phosphorylase inhibitory activity can be determined by the coupled xanthine oxidase method using inosine as the purine substrate (H. M. Kalckar, J.) Biol. Chem. 167 (1947) 429–443. Purine phosphoribosyltransferase activity is detected in the same assay using inosine 5'-phosphate as the substrate. Slow onset inhibitor binding can be determined using methods such as those described by Merkler et al., Biochemistry 29 (1990) 8358–8364. Parasite nucleoside hydrolase activity may be measured inter alia by methods disclosed in published PCT international patent application WO 97/31008 and the references cited therein.

The potency of the inhibitors of the invention provides important advantages over the prior art because of the relatively high activity of PNP in blood and mammalian tissue. As mentioned above the required dosage of 9-(3-pyridylmethyl)-9-deazaguanine may be of the order of 3.5 grams per dose for a human adult. The present invention provides the advantage that considerably lower quantities of the compounds are required. This allows cost saving and may also reduce unwanted side effects.

The amount of active ingredient to be administered can vary widely according to the nature of the patients and the nature and extent of the disorder being treated. Typically the dosage for an adult human will be in the range less than 1 to 1000 milligrams, preferably 0.1 to 100 milligrams. The active compound can be administered with a conventional pharmaceutical carrier and may be administered orally, by injection or topically.

The preferred route of administration is oral administration. For administration by this route the compounds can be formulated into solid or liquid preparations, eg tablets, capsules, powders, solutions, suspensions and dispersions. Such preparations are well known in the art as are other oral dosage forms not listed here. In a preferred embodiment the compounds of the invention are tableted with conventional tablet bases such as lactose, sucrose and corn starch together with a binder, a disintegration agent and a lubricant. These exipients are well known in the art. The binder may be for example corn starch or gelatin, the disintegrating agent may be potato starch or alginic acid and the lubricant may be magnesium stearate. Other components such as colouring agents and flavouring agents may be included.

Liquid forms for use in the invention include carriers such as water and ethanol, with or without other agents such as a pharmaceutically acceptable surfactant or suspending agent.

The compounds of the invention may also be administered by injection in a physiologically acceptable diluent such as water or saline. The diluent may comprise one or more of other ingredients such as ethanol, propylene glycol, an oil or a pharmaceutically acceptably surfactant.

Compounds of the invention may be applied to skin or mucous membranes. They may be present as ingredients in creams, preferably including a pharmaceutically acceptable solvent to assist passage through the skin or mucous membranes. Suitable cream bases are well known to those skilled in the art.

The compounds of the invention may be administered by means of sustained release systems for example they may be incorporated into a slowly dissolving tablet or capsule containing a solid or porous or matrix form from a natural or synthetic polymer.

EXAMPLES

The following examples further illustrate practice of the invention. Ratios of solvents are by volume.

Example 1

Preparation of (1S)-1,4-dideoxy-1-C-(4-hydroxypyrrolo[3,2-d]pyrimidin-7-yl)-1,4-imino-D-ribitol

Example 1.1.

A solution of 5-O-tert-butyldimethylsilyl-1,4-dideoxy-1,4-imino-2,3-O-isopropylidene-D-ribitol (Furneaux et al, Tetrahedron 53 (1997) 2915 and references therein) (2.0 g) in pentane (40 ml) was stirred with N-chlorosuccinimide (1.2 g) for 1h. The solids and solvent were removed and the residue was dissolved in dry tetrahydrofuran (40 ml) and cooled to −78° C. A solution of lithium tetramethylpiperidide (25 ml, 0.4 M in tetrahydrofuran) was added slowly dropwise. The resulting solution was then added via cannula to a solution of lithiated acetonitrile [prepared by the dropwise addition of acetonitrile (2.08 ml, 40 mmol) to a solution of butyl lithium (29.8 ml, 41.8 mmol) in dry tetrahydrofuran (50 ml) at −78° C., followed by stirring for 45 min and then addition of tetramethylpiperidine (0.67 ml, 4 mmol)] at −78° C. The reaction mixture was stirred for 15 min then quenched with water and partitioned between water and chloroform. The organic phase was dried and concentrated, and then chromatography afforded (1S)-5-O-tert-butyldimethylsilyl-1-C-cyanomethyl-1,4-dideoxy-1,4-imino-2,3-O-isopropylidene-D-ribitol (1) (0.83 g).

Example 1.2

A solution of the product from Example 1.1 (0.80 g) in dichloromethane (20 ml) containing di-tert-butyldicarbonate (0.59 g) was stirred at room temperature for 16 h. The solution was concentrated and then chromatography afforded (1S)-N-tert-butoxycarbonyl-5-O-tert-butyldimethylsilyl-1-C-cyanomethyl-1,4-dideoxy-1,4-imino-2,3-O-isopropylidene-D-ribitol (2) (0.89 g).

Example 1.3

To a solution of the product from Example 1.2 (0.88 g) in N,N-dimethylformamide (5 ml) was added tert-butoxy bis (dimethylamine)methane (1.5 ml) and the solution was heated at 65–70° C. for 1 h. Toluene (20 ml) was added and the solution was washed (×3) with water, dried and concentrated to dryness. The residue was dissolved in tetrahydrofuran/acetic acid/water (1:1:1 v/v/v, 40 ml) at room temperature. After 1.5 h chloroform (50 ml) was added and the mixture was washed with water (×2), aqueous sodium bicarbonate, and then dried and evaporated to dryness. Chromatography of the residue gave (1S)-N-tert-butoxycarbonyl-5-O-tert-butyldimethylsilyl-1-C-(1-cyano-2-hydroxyethenyl)-1,4-dideoxy-1,4-imino-2,3-O-isopropylidene-D-ribitol (3) (0.68 g)

Example 1.4

Glycine hydrochloride ethyl ester (0.76 g) and sodium acetate (0.9 g) were added to a stirred solution of the product from Example 1.3 (0.51 g) in methanol (10 ml). The mixture was stirred at room temperature for 16 h and then concentrated to dryness. Chromatography of the residue gave the (1S)-N-tert-butoxycarbonyl-5-O-tert-butyldimethylsilyl-1-C-[1-cyano-2-(ethoxycarbonylmethylamino) ethenyl]-1,4-dideoxy-1,4-imino-2,3-O-isopropylidene-D-ribitol (4) (0.48) g as a diastereomeric mixture.

Example 1.5

A solution of the product from Example 1.4 (0.28 g) in dry dichloromethane (12 ml) containing 1,8-diazabicyclo[5.4.0]undec-7-ene (1.5 ml) and benzyl chloroformate (0.74 ml) was heated under reflux for 8 h, then cooled and washed with dilute aqueous HCl, aqueous sodium bicarbonate, dried and concentrated. Chromatography of the residue afforded (1S)-1-C-[3-amino-1-N-benzyloxycarbonyl-2-ethoxycarbonyl-4-pyrrolyl]-N-tert-butoxycarbonyl-5-O-tert-butyldimethylsilyl-1,4-dideoxy-1,4-imino-2,3-O-isopropylidene-D-ribitol (5) (0.22 g).

Example 1.6

A solution of the product from Example 1.5 (0.22 g) in ethanol (10 ml) was stirred with 10% Pd/C (50 mg) in an atmosphere of hydrogen for 3 h. The solids and solvent were removed and the residue was dissolved in ethanol (10 ml) containing formamidine acetate (0.40 g) and the solution was heated under reflux for 8 h. The solvent was removed and chromatography of the residue gave (1S)-N-tert-butoxycarbonyl-5-O-tert-butyldimethylsilyl-1,4-dideoxy-1-C-[4-hydroxypyrrolo[3,2-d]pyrimidin-7-yl]-1,4-imino-2,3-O-isopropylidene-D-ribitol (6) (156 mg).

Example 1.7

A solution of the product from Example 1.6 (66 mg) in trifluoroacetic acid (3 ml) was allowed to stand at room temperature overnight. The solution was concentrated and a solution of the residue in water was washed (×2) with chloroform and then evaporated. The residue was dissolved in methanol and treated with Amberlyst A21 base resin until the solution was pH~7. The solids and solvent were removed and the residue was dissolved in water, treated with excess aqueous HCl and then lyophilized. Trituration of the residue with ethanol gave (1S)-1,4-dideoxy-1-C-(4-hydroxypyrrolo[3,2-d]pyrimidin-7-yl)-1,4-imino-D-ribitol (7) hydrochloride salt as a white solid (25 mg). Recrystallised from 90% ethanol, the crystalline solid darkened but did not melt below 300° C. NMR (300 MHz, $D_2O$ with DCl, δ ppm): $^{13}C$ (relative to internal acetone at 33.2 ppm) 58.1 (C-1'), 61.4 (C-5'), 68.8 (C-4'), 73.3 (C-3'), 76.7 (C-2'), 107.5 (q), 121.4

(q), 133.5 (C-2), 135.0 (q), 148.0 (C-6) and 155.4 (q); $^1$H (relative to internal acetone at 2.20 ppm), 3.90 (H-4'), 3.96 (m, H-5',5"), 4.44 (dd, H-3', $J_{2',3'}$ 5.4 Hz, $J_{3',4'}$ 3.2 Hz), 4.71 (dd, $J_{1',2'}$ 9.0 Hz, H-2'), 5.00 (d, H-1'), 8.00 (s, H-6) and 9.04 (s, H-2)

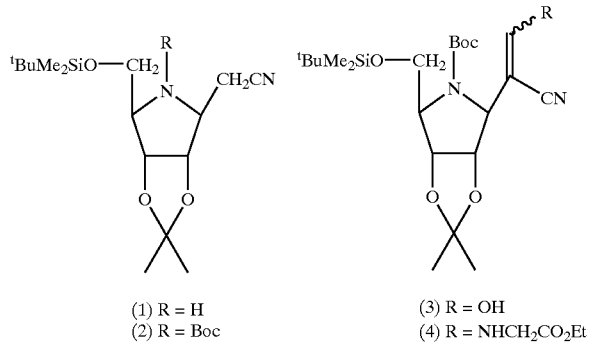

(1) R = H
(2) R = Boc
(3) R = OH
(4) R = NHCH$_2$CO$_2$Et

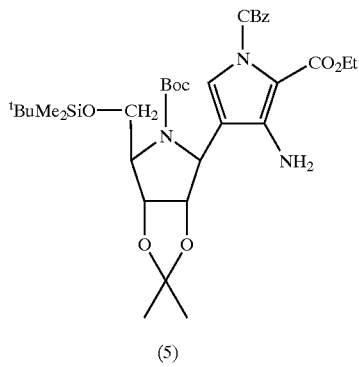

(5)

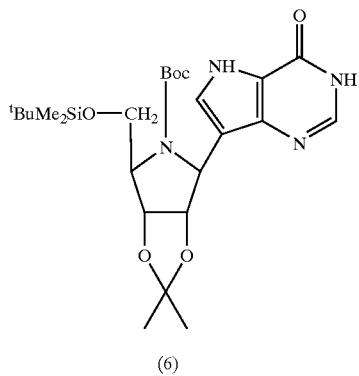

(6)

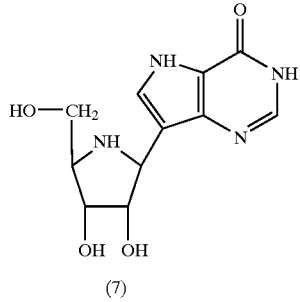

(7)

Example 2

Preparation of (1S)-1-C-(2-amino-4-hydroxypyrrolo[3,2-d]pyrimidin-7-yl)-1,4-dideoxy-1,4-imino-D-ribitol Example 2.1

A solution of (1S)-1-C-[3-amino-1-N-benzyloxycarbonyl-2-ethoxycarbonyl-4-pyrrolyl]-N-tert-butoxycarbonyl-5-O-tert-butyldimethylsilyl-1,4 dideoxy 1,4-imino-2,3-O-isopropylidene-D-ribitol (Example 1.5) (0.87 g) in ethanol was stirred with 10% Pd/C (100 mg) in an atmosphere of hydrogen for 1.5 h. The solids and solvent were removed to give a residue (0.61 g). To a solution of a portion of this residue (0.12 g) in dichloromethane (10 ml) at 0° C. was added a solution of benzoyl isothiocyanate in dichloromethane (31 mL in 1 ml). After 0.5 h the solution was warmed to room temperature and 1,8-diazabicyclo[5.4.0]undec-7-ene (80 mL) and methyl iodide (100 mL) were added. After another 0.5 h the reaction solution was applied directly to a silica gel column and elution afforded 0.16 g of (1S)-1-C-[3-(N-benzoyl-S-methylisothiocarbamoyl)amino-2-ethoxycarbonyl-4-pyrrolyl]-N-tert-butoxycarbonyl-5-O-tert-butyldimethylsilyl-1,4-dideoxy-1,4-imino-2,3-O-isopropylidene-D-ribitol.

Example 2.2

A solution of this S-methylisothiocarbamoylamino derivative, (0.20 g) in methanol saturated with ammonia was heated in a sealed tube at 95° C. for 16 h. The solvent was removed and chromatography of the residue afforded (1S)-1-C-[2-amino-4-hydroxypyrrolo[3,2-d]pyrimidin-7-yl]-N-tert-butoxycarbonyl-1,4-dideoxy-1,4-imino-2,3-O-isopropylidene-D-ribitol.

Example 2.3

A solution of this protected iminoribitol (64 mq) in trifluoroacetic acid was allowed to stand at room temperature for 16 h. The solvent was removed and a solution of the residue in aqueous methanol (1:1) was treated with Amberlyst A21 base resin until the pH of the solution was ~7. The solids and solvent were removed and a solution of the residue in water was treated with excess HCl and then concentrated to dryness. Trituration with ethanol gave (1S)-1-C-(2-amino-4-hydroxypyrrolo[3,2-d]pyrimidin-7-yl)-1,4-dideoxy-1,4-imino-D-ribitol hydrochloride salt (24 mg), which darkened at ca. 260° C. but did not melt below 300° C. NMR (300 MHz, D$_2$O with DCl, δ ppm): $^{13}$C (relative to internal acetone at 33.1 ppm) 58.0 (C-1'), 61.4 (C-5'), 68.6 (C-4'), 73.3 (C-3'), 76.3 (C-2'), 105.2 (q), 114.8 (q), 132.1 (C-6), 135.3 (q), 153.4 (q) and 156.4 (q); $^1$H (relative to internal acetone at 2.20 ppm) 3.87 (m, H-4'), 3.94 (m, H-5',5"), 4.40 (dd, $J_{2',3'}$ 5.0 Hz, $J_{3',4'}$ 3.2 Hz, H-3'), 4.65 (dd, , $J_{1',2'}$ 9.1 Hz, H-2'), 4.86 (d, H-1') and 7.71 (s, H-6).

Examples 3–24

The following compounds may be prepared according to methods disclosed in the general description:
3. (1R)-1-C-(4-hydroxypyrrolo[3,2-d]pyrimidin-7-yl)-1,4-imino-1,2,4-trideoxy-D-erythro-pentitol may be prepared from the product of Example 1 using Method (H)
4. (1S)-1-C-(4-hydroxypyrrolo[3,2-d]pyrimidin-7-yl)-1,4-imino-1,4,5-trideoxy-D-ribitol may be prepared from the product of Example 1 using Method (K).
5. (1S)-1,4-dideoxy-1-C-(4-hydroxypyrrolo[3,2-d]pyrimidin-7-yl)-1,4-imino-5-methylthio-D-ribitol may be prepared from the product of Example 1 using Method (K).
6. (1S)-1,4-dideoxy-1-C-(2,4-dihydroxypyrrolo[3,2-d]pyrimidin-7-yl)-1,4-imino-D-ribitol may be prepared from the product of Examples 1 or 2 using Method (M).
7. (1R)-1-C-(2,4-dihydroxypyrrolo[3,2-d]pyrimidin-7-yl)-1,4-imino-1,2,4-trideoxy-D-erythro-pentitol may be prepared from the product of Example 6 using Method (H).

8. (1S)-1-C-(2,4-dihydroxypyrrolo[3,2-d]pyrimidin-7-yl)-1,4-imino-1,4,5-trideoxy-D-ribitol may be prepared from the product of Example 6 using Method (K).
9. (1S)-1,4-dideoxy-1-C-(2,4-dihydroxypyrrolo[3,2-d]pyrimidin-7-yl)-1,4-imino-5-methylthio-D-ribitol may be prepared from the product of Example 6 using Method (K).
10. (1R)-1-C-(2-amino-4-hydroxypyrrolo[3,2-d]pyrimidin-7-yl)-1,4-imino-1,2,4-trideoxy-D-erythro-pentitol may be prepared from the product of Example 2 by Method (H).
11. (1S)-1-C-(2-amino-4-hydroxypyrrolo[3,2-d]pyrimidin-7-yl)-1,4-imino-1,4,5-trideoxy-D-ribitol may be prepared from the product of Example 2 by Method (K).
12. (1S)-1-C-(2-amino-4-hydroxypyrrolo[3,2-d]pyrimidin-7-yl)-1,4-dideoxy-1,4-imino-5-methylthio-D-ribitol may be prepared from the product of Example 2 using Method (K).
13. (1S)-1,4-dideoxy-1-C-(7-hydroxypyrazolo[4,3-d]pyrimidin-3-yl)-1,4-imino-D-ribitol may be prepared by Methods (D), (E) and (F).
14. (1R)-1-C-(7-hydroxypyrazolo[4,3-d]pyrimidin-3-yl)-1,4-imino-1,2,4-trideoxy-D-erythro-pentitol may be prepared from the product of Example 13 using Method (H).
15. (1S)-1-C-(7-hydroxypyrazolo[4,3-d]pyrimidin-3-yl)-1,4-imino-1,4,5-trideoxy-D-ribitol may be prepared from the product of Example 13 using Method (K).
16. (1S)-1,4-dideoxy-1-C-(7-hydroxypyrazolo[4,3-d]pyrimidin-3-yl)-1,4-imino-5-methylthio-D-ribitol may be prepared from the product of Example 13 using Method (K).
17. (1S)-1,4-dideoxy-1-C-(5,7-dihydroxypyrazolo[4,3-d]pyrimidin-3-yl)-1,4-imino-D-ribitol may be prepared from the product of Example 13 using Method (M).
18. (1R)-1-C-(5,7-dihydroxypyrazolo[4,3-d]pyrimidin-3-yl)-1,4-imino-1,2,4-trideoxy-D-erythro-pentiol may be prepared from the product of Example 17 using Method (H).
19. (1S)-1-C-(5,7-dihydroxypyrazolo(4,3-d]pyrimidin-3-yl)-1,4-imino-1,4,5-trideoxy-D-ribitol may be prepared from the product of Example 17 using Method (K).
20. (1S)-1,4-dideoxy-1-C-(5,7-dihydroxypyrazolo[(4,3-d]pyrimidin-3-yl)-1,4-imino-5-methylthio-D-ribitol may be prepared from the product of Example 17 using Method (K).
21. (1S)-1-C-(5-amino-7-hydroxypyrazolo[4,3-d]pyrimidin-3-yl)-1,4-dideoxy-1,4-imino-D-ribitol may be prepared using a variation of Method (D) in which the compound of Formula XIb or XIc is replaced by a corresponding compound in which the hydrogen atom in position 5 is replaced by protected amino group.
22. (1R)-1-C-(5-amino-7-hydroxypyrazolo[4,3-d]pyrimidin-3-yl)-1,4-imino-1,2,4-trideoxy-D-erythro-pentitol may be prepared from the product of Example 21 using Method (H).
23. (1S)-1-C-(5-amino-7-hydroxypyrazolo[4,3-d]pyrimidin-3-yl)-1,4-imino-1,4,5-trideoxy-D-ribitol may be prepared from the product of Example 21 using Method (K).
24. (1S)-1-C-(5-amino-7-hydroxypyrazolo[4,3-d]pyrimidin-3-yl)-1,4-dideoxy-1,4-imino-5-methylthio-D-ribitol may be prepared from the product of Example 21 using Method (K)

Example 25

Enzyme Inhibition Results

Example 25.1

Inhibition of purine nucleoside phosphorylases. Enzyme assays were conducted to assess the effectiveness of the products of Examples 1 and 2 (compounds Ib and Ic respectively) as inhibitors of purine nucleoside phosphorylase. The assays used human RBC and calf spleen purine nucleoside phosphorylase (ex Sigma, 90% pure) with inosine as substrate, in the presence of phosphate buffer, with detection of released hypoxanthine using xanthine oxidase coupled reaction.

Materials. Inosine was obtained from Sigma. Xanthine oxidase (EC 1.1.3.22, buttermilk), human erythrocyte (as a lyophilized powder) and bovine spleen (in 3.2 M ammonium sulfate) purine nucleoside phosphorylases (EC 2.4.2.1) were purchased from Sigma. Human purine nucleoside phosphorylases obtained as a powder was reconstituted in 100 mM sodium phosphate buffer (pH 7.4) and rapidly frozen and stored at –80° C. Kinetic experiments were performed on a Uvikon 933 double beam ultraviolet/visible spectrophotometer (Kontron Instruments, San Diego, Calif.).

Protein Concentrations. Protein concentrations for both isozymes were determined based on the quantative ultraviolet absorbance, using $E_{1cm}1\%=9.64$ at 280 nm [Stoelkler et al, Biochemistry, 32 (1978) 278] and a monomer moleculer weight of 32,000 [Williams et al, Nucleic Acids Res. 12 (1984) 5779].

Enzyme Assay. Enzymes were assayed spectrophotometrically using the coupled xanthine oxidase method [Kalckar, J. Biol. Chem. 167 (1947) 429; Kim et al, J. Biol. Chem., 243 (1968) 1763]. Formation of uric acid was monitored at 293 nm. A 40 mM inosine solution gave an absorbance change of 0.523 units at 293 m, upon complete conversion of inosine to uric acid and ribose 1-phosphate. Unless otherwise noted, the standard assay reaction contained: inosine (500 $\mu$M), potassium phosphate (50 mM, pH 7.5); xanthine oxidase (0.06 units) and purine nucleoside phosphorylase in a final volume of 1.0 mL.

One-Third-the-Sites Inhibition. Reaction mixtures of 6.7 nM bovine purine nucleoside phosphorylase containing varying amounts of compound Ib were pre-incubated at 30° C. for 1 hour. Reactions were initiated by addition of substrate (40 $\mu$M inosine, 3 times the $K_m$ value) and assayed at 30° C. The reaction containing 0.6 nM inhibitor (concentration ratio of [compound Ib]/[purine nucleoside phosphorylase]=0.09) showed 29% inhibition, that containing 1 nM inhibitor ([compound Ib])/ [purine nucleoside phosphorylase]=0.15) showed 44%, whereas the reaction containing 3 nM inhibitor ([compound Ib]/purine nucleoside phosphorylase]=0.44) had a rate decrease of 96%, and that containing 6 nM inhibitor ([compound Ib])/[purine nucleoside phosphorylate]=87%) showed 99% inhibition. These interactions are shown in FIG. 1.

Purine nucleoside phosphorylase is known to be a homotrimer with a catalytic site on each of the three protein subunits [Stoelkler et al, Biochemistry 32, (1978) 278]. When the concentration of enzyme subunits is 6.7 nM, 50% inhibition of purine nucleoside phosphorylase occurs at approximately 1.1 nM. This result demonstrates that compound Ib binds tightly and that binding of compound Ib to one site of the trimeric enzyme leads to complete inhibition.

Figure 2:
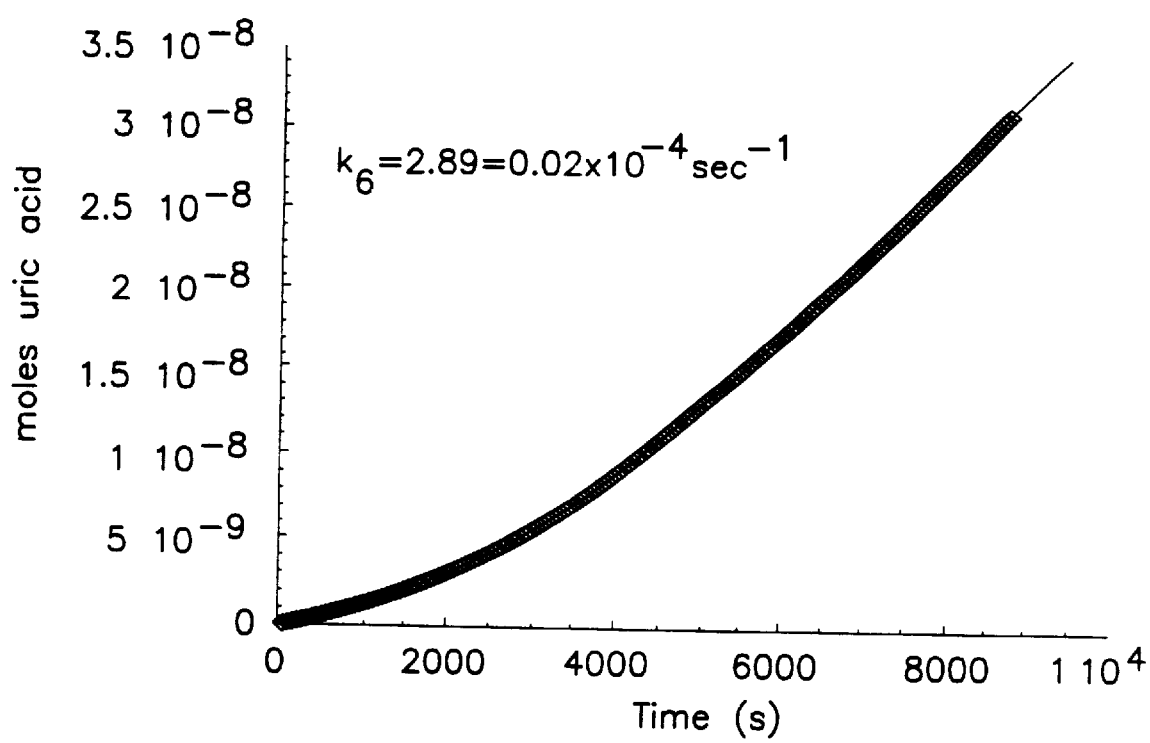
FIG. 2.

Activity Recovery from the Complex of Purine Nucleoside Phosphorylase with Compound Ib. Purine nucleoside phosphorylase (6.7 $\mu$M) and sufficient compound Ib (3 $\mu$M) to inhibit 96% of purine nucleoside phosphorylase activity were incubated at 30° C. for 1 hour. An aliquot of this solution was diluted 1000-fold into a buffered solution of 500 $\mu$M inosine containing xanthine oxidase (0.06 units). The production of uric acid was monitored over time and the progres curve was fit to the kinetic model of FIG. 2.

Dilution of inhibited purine nucleoside phosphorylase into a large volume of solution without inhibitor provided the rate of release of compound Ib from inhibited purine nucleoside phosphorylase. Under conditions of the experiment in FIG. 2, the time to achieve the new enzyme-inhibitor equilibrium is 5000 sec, an indication of a slow, tight-binding inhibitor (Morrison and Walsh, Advances Enzymol. 61 (1988) 201]. The rate contant $k_6$ is an estimate of the apparent first-order rate constant for dissociation of the complex under these experimental conditions and is $2.9 \times 10^{-4}$ sec$^{-1}$ in this example.

Inhibitory Mechanism. Slow, tight-binding inhibitors generally follow the kinetic mechanism [Morrison and Walsh, Advances Enzymol. 61 (1988) 201]:

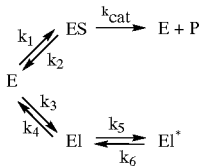

where EI is a rapidly formed, initial collision complex of purine nucleoside phosphorylase (E) and compound Ib (I) that slowly isomerizes to a tighter complex EI*. Product formation curves are described by the following integrated rate equation 1:

$$P = v_s t + (v_o - v_s)(1 - e^{-k\,t})/k \qquad 1$$

where P is the amount of product hypoxanthine (observed as uric acid in the present assay system), t is time, $v_o$ is the initial rate, $v_s$ is the final steady-state rate and k is the overall (observed) rate constant given by equation 2:

$$k = k6 + k5[(I/K_i)/(1 + (S/K_m) + (I/K_i))] \qquad 2$$

where $K_m$ is the Michaelis complex for purine nucleoside phosphorylase, S is inosine concentration, I is the concentration of compound Ib and $K_i$ is as described below. The rate of formation of the tightly bound complex is k5 and the rate of its dissociation is k6. $K_i$, the inhibition constant for standard competitive inhibition (which influences $v_o$) and $K_i^*$, the overall inhibition constant (which influences $v_s$), are defined as:

$$K_i = k4/k3$$

$$K_i^* = K_i[k_6/(k_5 + k_6)]$$

Figure 3:
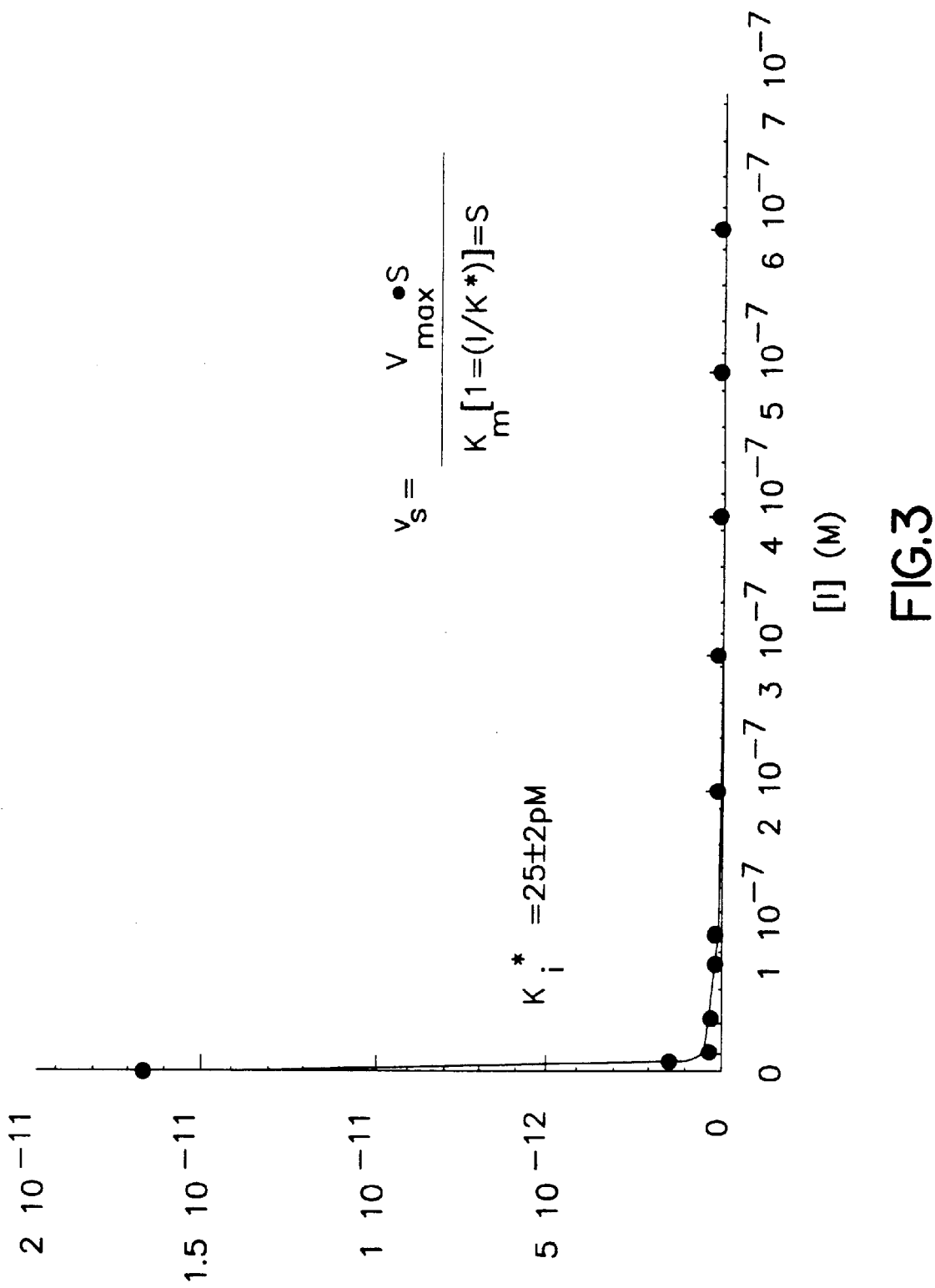
FIG. 3.

Determination of $K_i^*$. $K_i^*$ was determined by measuring $v_s$ for reactions at a range of inhibitor concentrations, plotting $v_s$ vs [I] and fitting the curve to the competive inhibition equation 3:

$$v_s = V_{max} S/[K_m(1 + I/K_i^*) + S] \qquad 3$$

where $v_{max}$ is the uninhibited reaction rate for purine nucleoside phosphorylase, and the remaining terms are described above. The result of this analysis indicates an overall effective inhibition constant ($K_i^*$) of $2.5 \pm 0.2 \times 10^{-11}$ M ($25 \pm 2$ pM) for compound Ib (FIG. 3).

Approximation of $K_i$, $k_5$ and $k_6$. Calculation of $K_i$ directly from $v_o$ and the competitive inhibition equation (above) is difficult for compound Ib because $v_o$ changes very little as a function of I at inhibitor concentrations which cause complete inhibition following slow onset. This result establishes that the initial dissociation constant $K_i$ is much greater than the equilibrium dissociation constant $K_i^*$.

Figure 4:
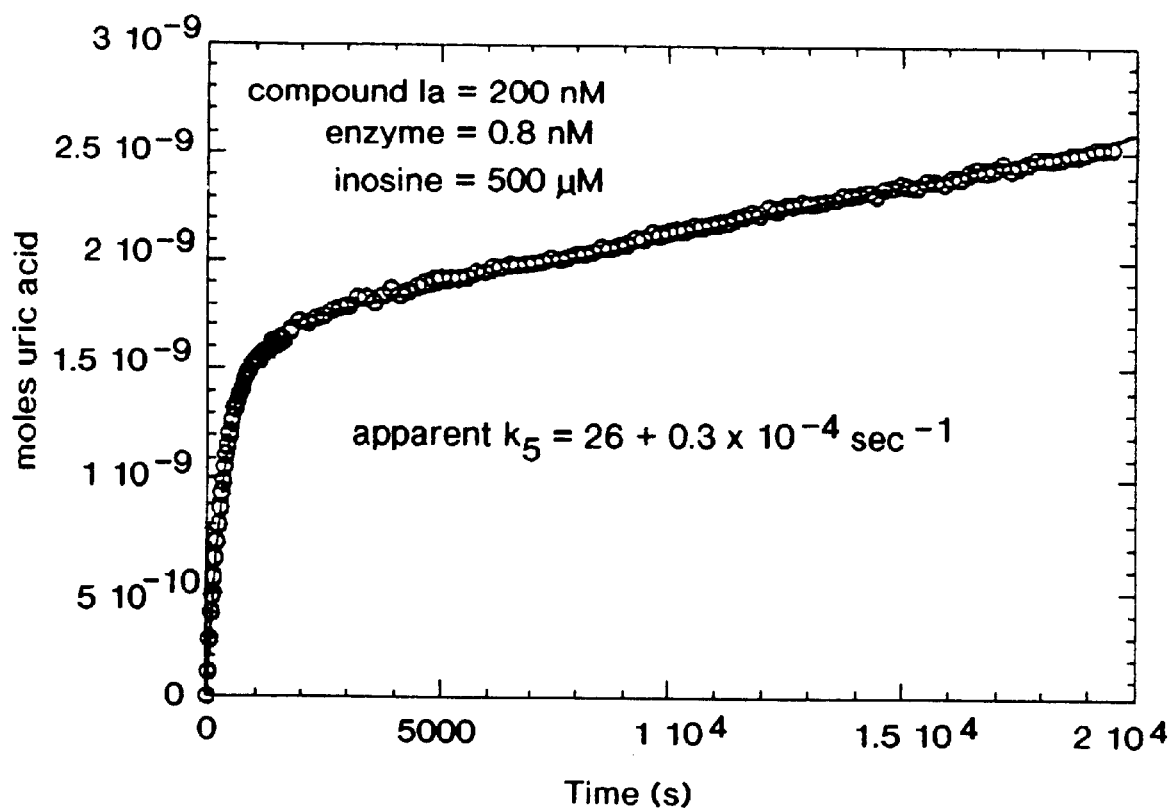
FIG. 4.

Approximations of $k_5$ and $K_i$ were calculated from k (values obtained from curve fits of equation 1, FIG. 4) by using equation 2. Using the knowledge that $k_6 << k_5[(I/K_i)/(1+(A/K_m)+(I/K_i)]$, equation 2 can be rearranged so that a double reciprocal plot of 1/k vs 1/[I] gives a straight line with y intercept=$1/k_5$ and x intercept of $-(1/k_5)/[K_i/k_5)*(A/K_m))$]. Substitution of these values into equation 2 give an approximation for $k_6$. FIG. 4 demonstrates the slow-onset, tight-binding inhibition which occurs when a small concentration of enzyme (0.8 nM) competes for 200 nM compound Ib in the presence of 500 $\mu$M inosine. Under these conditions the apparent first order rate constant for onset of inhibition in FIG. 4 was $26 \times 10^{-4}$ sec$^{-1}$.

The result of FIG. 4 demonstrates that even at inosine concentrations over 100 times that present in human serum or tissues, compound Ib can give 99% inhibition of the enzyme after several minutes of slow-onset inhibition. Based on analyses of experiments of the type shown in FIGS. 1–4, the experimentally estimated dissociation constants and rates for the bovine purine nucleoside phosphorylase with compound Ib are:

$K_m = 15\ \mu M$ $K_i = 19 \pm 4$ nM $K_i^* = 25 \pm 2$ pM $k_5 = 1.4 \pm 0.2 \times 10^{-2}$ sec$^{-1}$ $k_6 = 1.8 \pm 0.5 \times 10^{-5}$ sec$-1$ Inhibition of Human Purine Nucleoside Phosphorylase. Studies similar to those described above for the interaction of bovine purine nucleoside phosphorylase were conducted with purine nucleoside phosphorylase (PNP) from human erythrocytes. The values for the overall inhibition constant, $K_i^*$, for the interaction of human and bovine PNP with compound Ib are:

| enzyme | $K_i^*$, compound Ib | $K_i^*$, compound Ic |
| --- | --- | --- |
| human PNP | 72 ± 26 pM | 29 ± 8 pM |
| bovine PNP | 23 ± 5 pM | 30 ± 6 pM |

The compound Ic is a more efficient inhibitor for the human enzyme than compound Ib, but compound Ib is slightly more efficient at inhibiting the bovine enzyme. Compounds Ib and Ic are more efficient at inhibiting both PNP enzymes than previously reported compounds.

Summary of Compounds Ib and Ic as Inhibitors of Purine Nucleoside Phosphorylases. Inhibitors usually function by binding at every catalytic site to cause functional inhibition in living organisms. The one-third-the-sites inhibition and the slow-onset tight-binding inhibition described above indicate that compounds Ib and Ic are very potent inhibitors of purine nucleoside phosphorylases able to function in the presence of a large excess of substrate.

The methods for the determination of the kinetic constants are given in detail in Merkler, D. J., Brenowitz, M., and Schramm, V. L. Biochemistry 29 (1990) 8358–8364.

Example 25.2

Figure 5A:
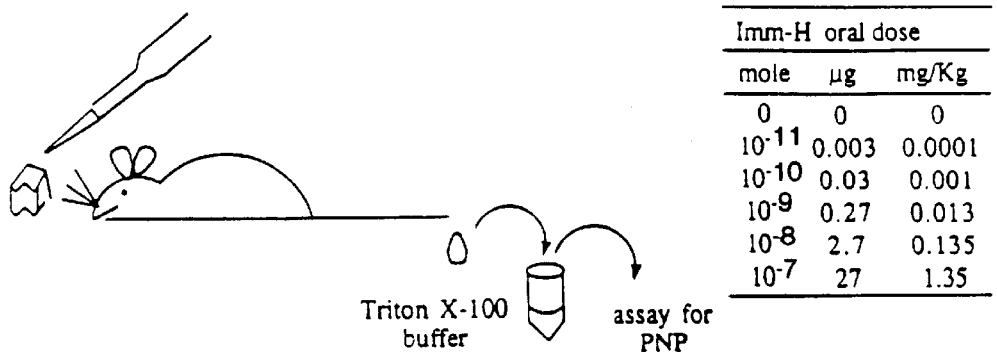
FIGS. 5A–5C.
Figure 5B:
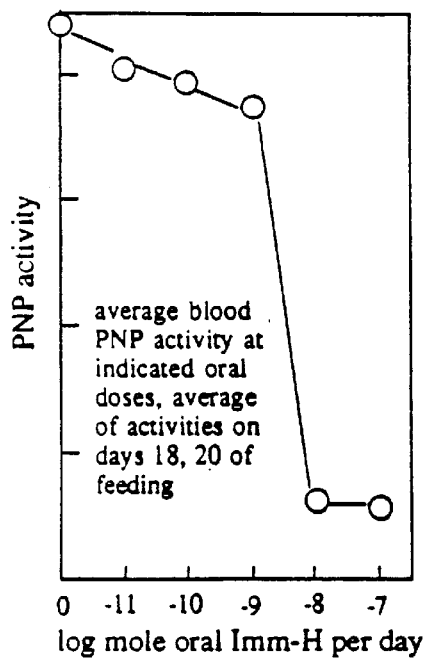
Figure 5C:
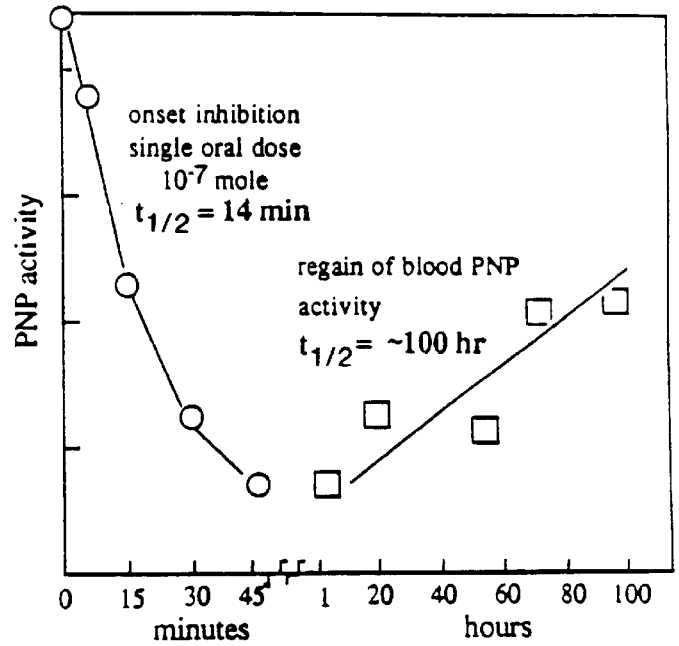

Oral Availability and in vivo Efficacy of Compound Ib as a PNP Inhibitor. A single oral dose of $10^{-7}$ mole of Compound Ib (27 $\mu$g) was administered with food to a young adult male mouse. Blood samples were collected from the tail at times indicated in FIG. 5. Dilution of blood into saline containing 0.2% Triton X-100 (final concentration 0.15%) resulted in lysis of blood cells and release of enzyme. PNP activity was measured with inosine and phosphate as substrates as indicated above. The results establish that Compound Ib is absorbed into the blood and taken up by blood cells to cause PNP inhibition with a half-time ($t_{1/2}$) of 14 minutes. Blood samples were taken for an extended time and analyzed for PNP activity to determine the biological $t_{1/2}$ for Compound Ib for inhibitors of blood PNP. The activity of blood PNP recovered with a $t_{1/2}$ of 100 hours. These results establish that Compound Ib is orally available and has an extended period of biological effectiveness. These tests establish that the compounds described herein have favorable pharmacological lifetimes.

Figure 6A:
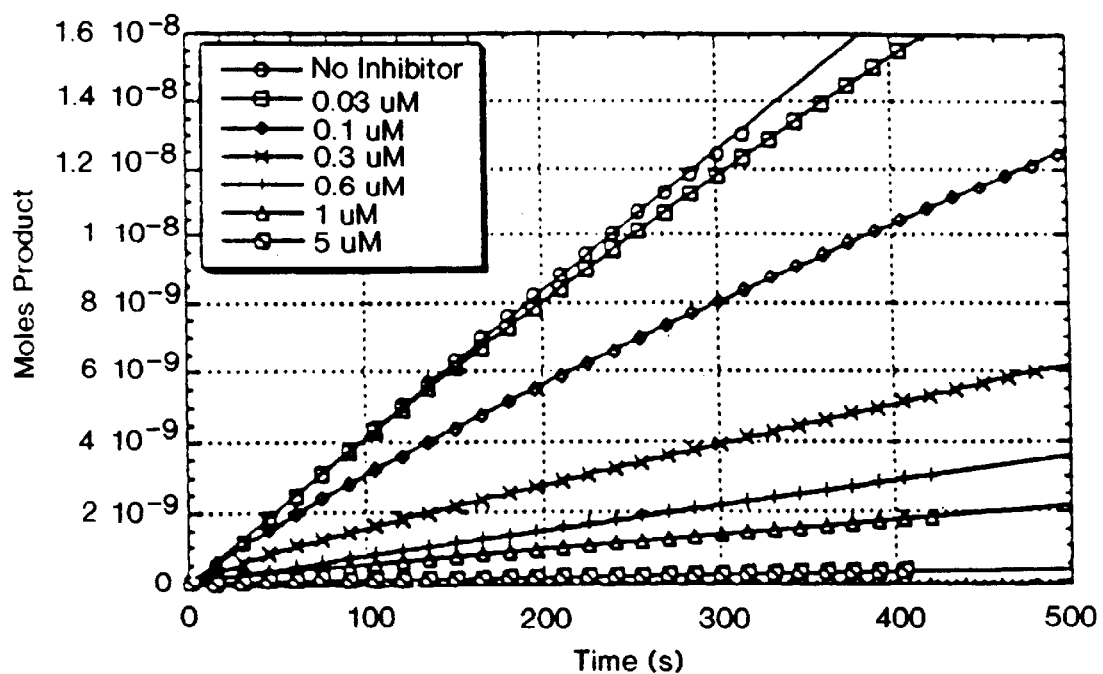
Figure 6B:
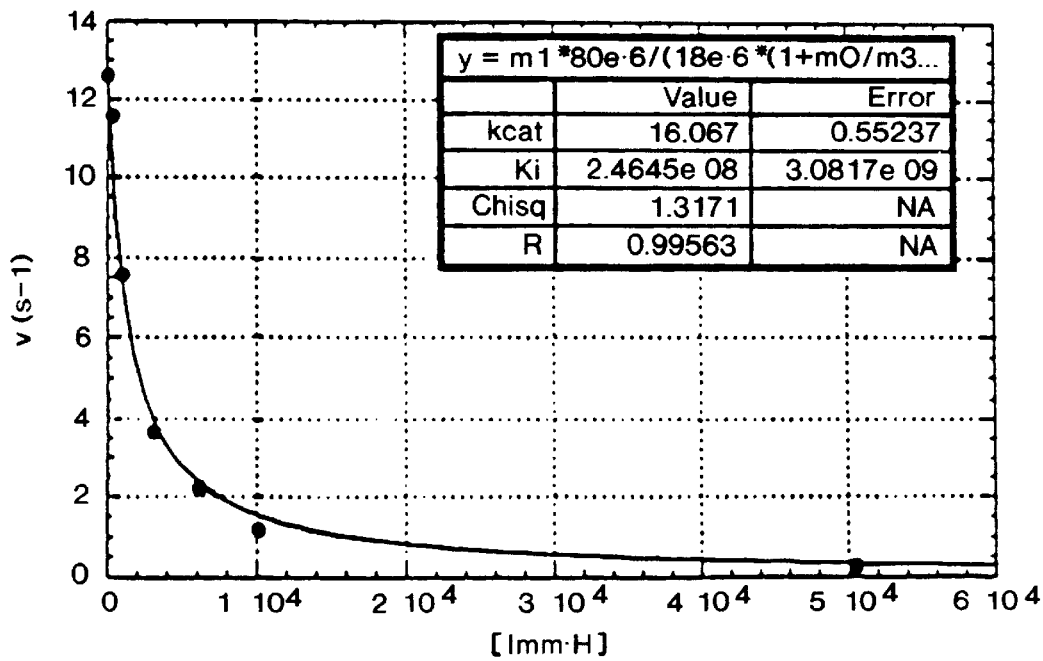

Inhibition of Protozan Nucleoside Hydrolases by Compounds Ib and Ic. Protozan parasites use the hydrolysis of purine nucleosides such as inosine to provide purine bases such as hypoxanthine to provide essential precursors for RNA and DNA synthesis. Protozoan parasites are purine auxotrophs. Using inhibition methods similar to those described above, a nucleoside hydrolase from *Crithidia fasciculata* [Parkin, et al, J Biol, Chem. 266 (1991) 20658] and a nucleoside hydrolase from *Trypanosoma brucei brucei* [Parkin, J. Biol. Chem. (1996) 21713] were tested for inhibition by compounds Ib and Ic. The inhibition of nucleoside hydrolase from *C. fasciculata* by Compound Ib is exemplified in FIG. 6. Similar studies indicated that Coumpound Ib and Ic are nanamolar inhibitors for nucleoside hydrolases from *C. fasciculata* and from *T. brucei brucei*. Compound Ic (A=CH, B=$NH_2$, D=H, X=OH, Y=H, Z=OH) is a nanamolar inhibitor of both enzymes and Compound Va (OR=$NH_2$, z'=OH, $CO_2$Bu=H or $H_2$, and the isopropylidine group removed to form two hydroxyl groups) is also a nanamolar inhibitor of both enzymes. The results are summarised below.

| | $K_i$ Values (nM) | | | |
|---|---|---|---|---|
| enzyme source | Compound Ia[a] | Compound Ib[b] | Compound Ic[b] | Compound Va[b] |
| nucleoside hydrolase *C. fasciculata* | 42 ± 2 nM | 40 nM | 7 nM | 3 nM |
| nuceloside hydrolase *T. brucei brucei* | 24 ± 3 nM | 108 nM | 0.9 nM | 23 nM |

[a]the average of multiple determinations and associated errors.
[b]single determination of $K_i$.

The inhibitors bind in direct competition with substrate, therefore the $K_i$ inhibition constants are direct competitive inhibition values. The compounds provide sufficient inhibition to the purine nucleoside hydrolases to inhibit protozoan parasites at readily accessible pharmacological doses.

The methods and materials used are as described in published PCT international application WO 97/31008 using p-nitrophenyl riboside as substrate.

Example 25.3

Figure 7:
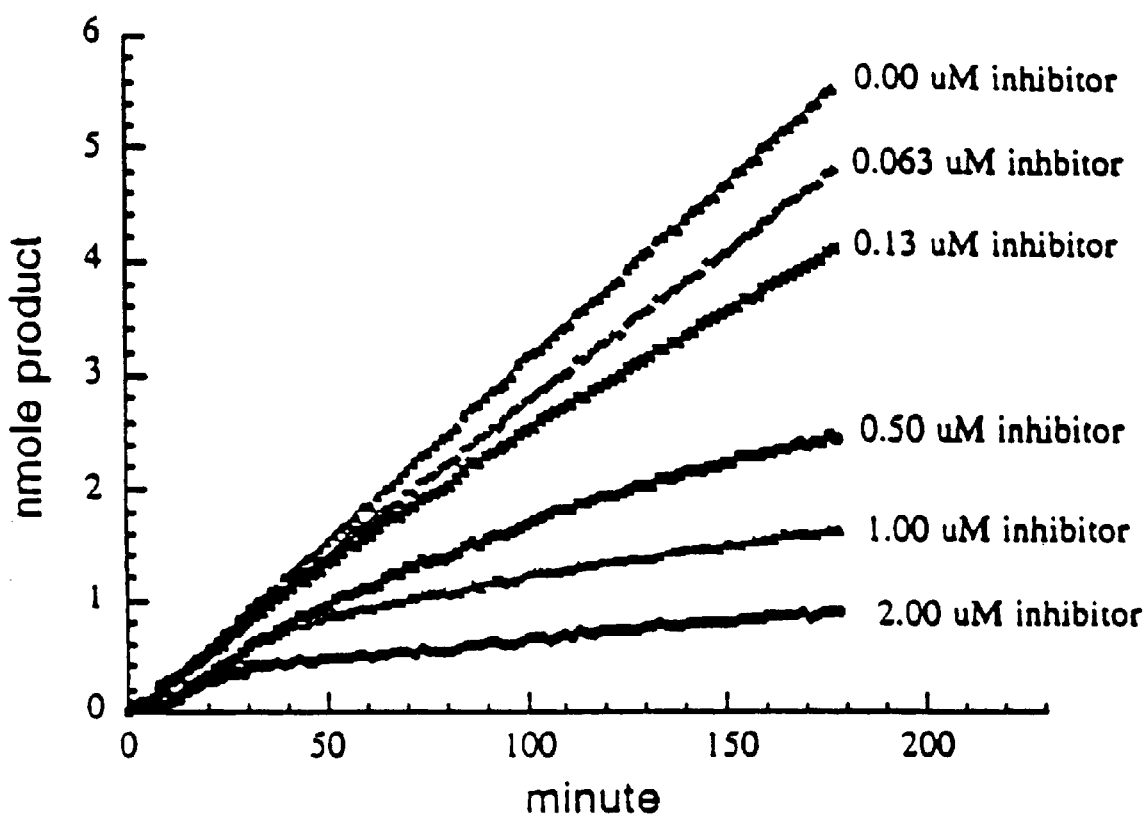
FIG. 7.
Figure 8:
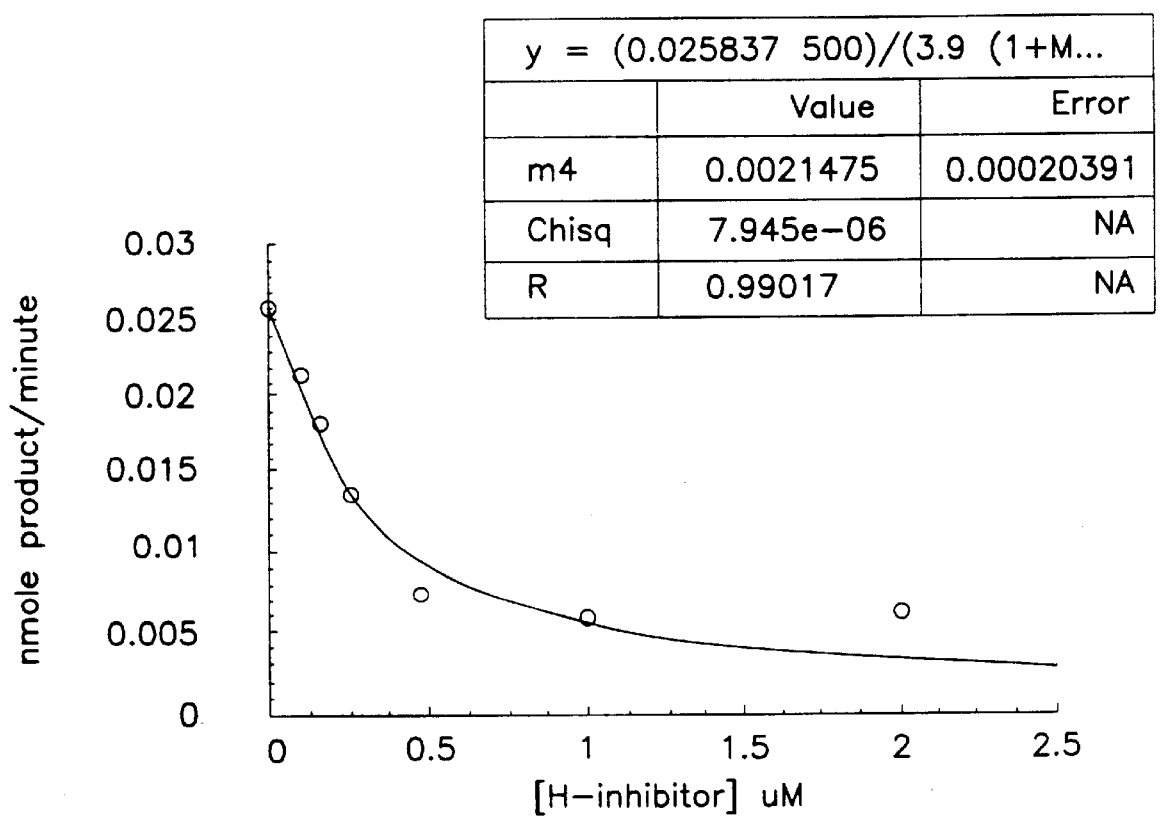
FIG. 8.

Inhibition of Purine Phosphoribisyl Transferases (PPRT) by 5'-Phosphates of Compounds Ib and Ic. Protozoan parasites, human tissues and tumors use PPRT for salvage of purine bases. Interruption of PPRT activity is expected to disrupt purine metabolism in these systems. 5'-phosphorylated Compounds I and Ic were anlyzed for inhibition of PPRT from human and malarial origins. The slow-onset inhibition curve for the 5'-phosphate of Compound Ib with malaria PPRT is illustrated in FIG. 7. The $K_i^*$ determination for the 5'-phosphate of Compound Ib with malarial PPRT is shown in FIG. 8. Analysis of both human and malarial enzymes with the 5'-phosphates of Compounds Ib and Ic are summarized below.

| enzyme source | Compound Ib-5'-phosphate | | Compound Ic-5'-phosphate | |
|---|---|---|---|---|
| | $K_i$ | $K_i^*$ | $K_i$ | $K_i^*$ |
| PPRT human | 40 nM | 3 nM | 14 nM | 8 nM |
| PPRT malaria | 33 nM | 3 nM | 48 nM | slow onset not observed |

Full inhibition studies indicated that the inhibitors are competitive with IMP. The nanamolar inhibition constants for both inhibitors with both enzymes are readily accessible pharmacologic doses of these inhibitors. It is anticipated that the nucleoside kinase activities of human and/or parasitic organisms will convert one or more of the compounds described herein to the respective 5'-phosphates. These compounds thereby provide precursors for pharmacologic doses of the 5'-phosphates for intracellular interruption of PPRT activity. The cellular uptake of Compounds I and Ic have been documented with mice and with human red cells.

Example 26

Tablet 4 grams of the product of Example 1 is mixed with 96 grams of lactose and 96 grams of starch. After screening and mixing with 2 grams of magnesium stearate, the mixture is compressed to give 250 milligram tablets.

Example 27

Gelatin Capsule

Ten grams of the product of Example 1 is finely ground and mixed with 5 grams of talc and 85 grams of finely ground lactose. The powder is filled into hard gelatin capsules.

Example 28

Preparation of (1R)-1,2,4-trideoxy-1-C-(4-hydroxypyrrolo[3,2-d]pyrimidin-7-yl)-1,4-imino-D-erythro-pentitol Example 28.1

A solution of (1S)-5-O-tert-butyldimethylsilyl-1-C-cyanomethyl-1,4-dideoxy-1,4-imino-2,3-O-isopropylidene-D-ribitol (1.93 g) in trifluoroacetic acid (20 ml) was allowed to stand at room temperature overnight. The solution was concentrated and a solution of the residue in water was washed (×2) with chloroform and then evaporated to afford (1S)-1-C-cyanomethyl-1,4-dideoxy-1,4-imino-D-ribitol (1.0 g) as the trifluoroacetic acid salt.

Example 28.2

A solution of the crude product from Example 3.1 (1.0 g) in methanol (20 ml) containing di-tert-butyldicarbonate (2.09 g) was adjusted to neutral pH by the addition of triethylamine and stirred at room temperature for 16 h. The solution was concentrated and then chromatography afforded (1S)-N-tert-butoxycarbonyl-1-C-cyanomethyl-1,4-dideoxy-1,4-imino-D-ribitol (0.80 g).

Example 28.3

1,3-Dichloro-1,1,3,3-tetraisopropyldisiloxane (0.9 ml) was added dropwise to a solution of the product from Example 3.2 (0.8 g) and imidazole (0.70 g) in N,N-dimethylformamide (10 ml) at 0° C. The resulting solution was allowed to warm to room temperature, diluted with toluene, washed with water (×3), dried, concentrated and then chromatography afforded (1S)-N-tert-butoxycarbonyl-1-C-cyanomethyl-1,4-dideoxy-1,4-imino -3,5-O-(1,1,3,3-tetraisopropyldisiloxan-1,3-diyl)-D-erythro-pentitol (1.4 g).

Example 28.4

A solution of the product from Example 3.3 (1.5 g) in toluene (20 ml) containing thiocarbonyldiimidazole (0.9 g) was stirred at 90° C. for 2 h. The solution was concentrated and then chromatography afforded (1S)-N-tert-butoxycarbonyl-1-C-cyanomethyl-1,4-dideoxy-2-O-[imidazole(thiocarbonyl)]-1,4-imino-3,5-O-(1,1,3,3-tetraisopropyldisiloxan-1,3-diyl)-D-erythro-pentitol (1.8 g).

Example 28.5

To a solution of the product from Example 28.4 (1.8 g) in toluene (50 ml) was added tri-n-butyltin hydride (1.0 ml) and the solution was heated at 80° C. for 3 h. The solution was concentrated and then chromatography afforded (1S)-N-tert-butoxycarbonyl-1-C-cyanomethyl-1,2,4-trideoxy-1,4-imino-3,5-O-(1,1,3,3-tetraisopropyldisiloxan-1,3-diyl)-D-erythro-pentitol (0.74 g).

Example 28.6

To a solution of the product from Example 3.5 (0.74 g) in N,N-dimethylformamide (10 ml) was added tert-butoxy-bis(dimethylamino)methane (1.5 ml) and the solution was heated at 65–70° C. for 1 h. Toluene (20 ml) was added and the solution was washed (×3) with water, dried and concentrated to dryness. The residue was dissolved in tetrahydrofuran/acetic acid/water (1:1:1 v/v/V, 40 ml) at room temperature. After 1.5 h, chloroform (50 ml) was added and the mixture was washed with water (×2), aqueous sodium bicarbonate, and then dried and evaporated to dryness. Chromatography of the residue gave (1R)-N-tert-butoxycarbonyl-1-C-(1-cyano-2-hydroxyethenyl)-1,2,4-trideoxy-1,4-imino-3,5-O-(1,1,3,3-tetraisopropyldisiloxan-1,3-diyl)-D-erythro-pentitol (0.68 g).

Example 28.7

Glycine hydrochloride ethyl ester (0.90 g) and sodium acetate (1.0 g) were added to a stirred solution of the product from Example 3.6 (0.68 g) in methanol (10 ml). The mixture was stirred at room temperature for 16 h and then concentrated to dryness. Chromatography of the residue gave the (1R)-N-tert-butoxycarbonyl-1-C-[1-cyano-2-(ethoxycarbonylmethylamino)ethenyl]-1,2,4-trideoxy-1,4-imino-3,5-O-(1,1,3,3-tetraisopropyldisiloxan-1,3-diyl)-D-erythro-pentitol (0.80 g) as a diastereomeric mixture.

Example 28.8

A solution of the product from Example 3.7 (0.80 g) in dry dichloromethane (20 ml) containing 1,8-diazabicyclo[5.4.0] undec-7-ene (3.6 ml) and benzyl chloroformate (1.7 ml) was heated under reflux overnight, then cooled and washed with dilute aqueous HCl and then aqueous sodium bicarbonate, dried and concentrated. Chromatography of the residue afforded (1R)-1-C-[3-amino-1-N-benzyloxycarbonyl-2-ethoxycarbonyl-4-pyrrolyl]-N-tert-butoxycarbonyl-1,2,4-trideoxy-1,4-imino-3,5-O-(1,1,3,3-tetraisopropyldisiloxan-1,3-diyl)-D-erythro-pentitol (0.70 g).

Example 28.9

A solution of the product from Example 28.8 (0.28 g) in ethanol (10 ml) was stirred with formamidine acetate (0.50 g) under reflux for 8 h. The solvent was removed and chromatography of the residue gave (1R)-N-tert-butoxycarbonyl-1,2,4-trideoxy-1-C-(4-hydroxypyrrolo[3,2-d]pyrimidin-7-yl)-1,4-imino-3,5-O-(1,1,3,3-tetraisopropyldisiloxa-1,3-diyl)-D-erythro-pentitol (120 mg).

Example 28.10

A solution of the product from Example 28.9 (120 mg) in trifluoroacetic acid (2 ml) was allowed to stand at room temperature overnight. The solution was concentrated and a solution of the residue in water was washed (×2) with chloroform and then evaporated. The residue was dissolved in tetrahydrofuran and treated with tetrabutylammonium fluoride trihydrate (200 mg) and stirred for 1 h. The solvent was evaporated and chromatography gave a residue which was redissolved in methanolic HCl. The resulting precipitate was filtered to afford (1R)-1,2,4-trideoxy-1-C-(4-hydroxypyrrolo[3,2-d]pyrimidin-7-yl)-1,4-imino-D-erythro-pentitol hydrochloride salt as a white solid (17 mg) which darkened but did not melt below 300° C. NMR (300 MHz, $D_2O$, d ppm): $^{13}C$ 38.8 (C-2'), 53.4 (C-1'), 59.3 (C-5'), 69.1 (C-4'), 71.5 (C-3'), 107.6 (q), 118.6 (q), 130.4 (C-2), 135.9 (q), 144.6 (C-6), and 153.7 (q); $^1H$ 2.69 (dd, J 14.3 Hz, J 6.4 Hz, H-2'), 2.60 (ddd, J 14.3 Hz, J 12.2 Hz, J 5.7 Hz, H-2"), 3.87 (m, 3H, H-4', H-5'), 4.57 (m, 1H, H-3'), 5.26 (dd, 1H, J 12.1 Hz, J 6.4 Hz, H-1'), 7.80 (s, H-6) and 8.65 (s, H-2). HRMS ($MH^+$) calc. for $C_{11}H_{14}N_4O_3$: 251.1144; found: 251.1143.

Example 29

Preparation of (1R)-1-C-(2-amino-4-hydroxypyrrolo [3,2-d]pyrimidin-7-yl)-1,2,4-trideoxy-1,4-imino-D-erythro-pentitol Example 29.1

A solution of (1R)-1-C-[3-amino-1-N-benzyloxycarbonyl-2-ethoxycarbonyl-4-pyrrolyl]-N-tert-butoxycarbonyl-1,2,4-trideoxy-1,4-imino-3,5-O-(1,1,3,3-tetraisopropyldisiloxan-1,3-diyl)-D-erythro-pentitol (Example 28.8) (0.78 g) in ethanol (10 ml) was stirred with 10% Pd/C (100 mg) in an atmosphere of hydrogen for 1.5 h. The solids and solvent were removed to give a residue (0.62 g). To a solution of this residue in dichloromethane (10 ml) at 0° C. was added a solution (4.8 ml) of benzoyl isothiocyanate in dichloromethane (0.30 ml in 10 ml). After 0.5 h, the solution was warmed to room temperature and 1,8-diazabicyclo[5.4.0]undec-7-ene (0.32 ml) and methyl iodide (0.70 ml) were added. After another 0.5 h the reaction solution was applied directly to a silica gel column and elution afforded 0.67 g of (1R)-1-C-[3-(1-benzamido-1-methylthiomethyleneamino)-2-ethoxycarbonyl-4-pyrrolyl]-N-tert-butoxycarbonyl-1,2,4-trideoxy-1,4-imino-3,5-O-(1,1,3,3-tetraisopropyldisiloxan-1,3-diyl)-D-erythro-pentitol.

Example 29.2

A solution of the product from Example 29.1 (0.67 g) in methanol saturated with ammonia (20 ml) was heated in a sealed tube at 105° C. for 16 h. The solvent was removed and chromatography of the residue afforded (1R)-1-C-(2-amino-4-hydroxypyrrolo[3,2-d]pyrimidin-7-yl)-N-tert-butoxycarbonyl-1,2,4-trideoxy-1,4-imino-3,5-O-(1,1,3,3-tetraisopropyldisiloxan-1,3-diyl)-D-erythro-pentitol (0.30 g).

Example 29.3

A solution of the product from Example 29.2 (300 mg) in trifluoroacetic acid (5 ml) was allowed to stand at room temperature for 16 h. The solvent was removed and the residue was dissolved in tetrahydrofuran, treated with tetrabutylammonium fluoride trihydrate (200 mg) and stirred for 1 h. The solvent was removed and the residue was dissolved in methanol (5.0 ml) and acetyl chloride (0.75 ml) was added dropwise and the reaction allowed to stand at room temperature for 16 h. The reaction was diluted with ether (25 ml) and the resulting crystals were filtered to afford (1R)-1-C-(2-amino-4-hydroxypyrrolo[3,2-d]pyrimidin-7-yl)-1,2,4-trideoxy-1,4-imino-D-erythro-pentitol hydrochloride salt (89 mg), which did not melt below 300° C. NMR (300 MHz, D$_2$O d ppm): $^{13}$C 38.8 (C-2'), 53.4 (C-1'), 59.3 (C-5'), 69.1 (C-4'), 71.5 (C-3'), 107.6 (q), 118.6 (q), 130.4 (C-2), 135.9 (q), 144.6 (C-6), and 153.7 (q); $^1$H 2.69 (dd, 1H, J 14.3 Hz, J 6.3 Hz, H-2'), 2.63 (ddd, 1H, J 14.1 Hz, J 12.3 Hz, J 5.7 Hz, H-2"), 3.88 (m, 3H, H-4', H-5'), 4.55 (m, 1H, H-3'), 5.14 (dd, 1H, J 12.2 Hz, J 6.3 Hz, H-1'), and 7.63 (s, H-6).

Example 30

Preparation of (1S)-1,4,5-trideoxy-1-C-(4-hydroxypyrrolo[3,2-d]pyrimidin-7-yl)-1,4-imino-D-ribitol hydrochloride salt

Example 30.1

A solution of the product from Example 1.5 (0.45 g) in dichloromethane (10 ml) was treated with triethylamine (0.45 ml), 4-dimethylaminopyridine (20 mg) and then methanesulfonyl chloride (0.1 ml). The solution was stirred for 1 h and then washed with 2M aq HCl, aq bicarbonate and processed conventionally. The crude product was dissolved in toluene (10 ml) containing tetrabutylammonium bromide (1.55 g) and the solution was heated at 100° C. for 2 h. The cooled solution was washed with water, and processed to give, after chromatography, (1S)-1-C-(3-amino-1-N-benzyloxycarbonyl-2-ethoxycarbonyl-4-pyrrolyl)-N-tert-butoxycarbonyl-5-bromo-1,4,5-trideoxy-1,4-imino-2,3-O-isopropylidene-D-ribitol (0.27 g).

Example 30.2

A solution of the product from Example 30.1 (0.27 g) in ethanol (10 ml) containing triethylamine (0.19 ml) was stirred with 20% Pd(OH)$_2$/C (0.1 g) in a hydrogen atmosphere for 16 h. The solids and solvent were removed and chromatography afforded (1S)-1-C-(3-amino-2-ethoxycarbonyl-4-pyrrolyl)-N-tert-butoxycarbonyl-1,4,5-trideoxy-1,4-imino-2,3-O-isopropylidene-D-ribitol (0.15 g).

Example 30.3

A solution of the product from Example 30.2 (75 mg) in ethanol containing formamidine acetate (0.15 g) was heated under reflux for 4 h. The solvent was removed and chromatography afforded (1S)-N-tert-butoxycarbonyl-1,4,5-trideoxy-1-C-[4-hydroxypyrrolo[3,2-d]pyrimidin-7-yl]-1,4-imino-2,3-O-isopropylidene-D-ribitol (69 mg).

Example 30.4

The product from Example 30.3 (69 mg) was dissolved in trifluoroacetic acid (5 ml) and the solution was allowed to stand at room temperature for 16 h. The solvent was removed and a solution of the residue in 50% aqueous ethanol (10 ml) was treated with Amberlyst A21 base resin until the pH was ~7. The solids and solvent were removed and the residue was treated with excess aqueous HCl and lyophilized to give (1S)-1,4,5-trideoxy-1-C-(4-hydroxypyrrolo[3,2-d]pyrimidin-7-yl)-1,4-imino-D-ribitol hydrochloride salt (46 mg). $^{13}$C NMR (75 MHz, D$_2$O with DCl, d ppm): 155.6 (C), 147.1 (CH), 137.4 (C), 132.6 (CH), 121.0 (C), 108.2 (C), 76.5 (C-3), 75.6 (C-2), 63.2 (C-4), 58.2 (C-1), 18.1 (C-5).

Example 31

Preparation of (1S)-1-C-(2-amino-4-hydroxypyrrolo[3,2-d]pyrimidin-7-yl)-1,4,5-trideoxy-1,4-imino-D-ribitol hydrochloride salt.

Example 31.1

A solution of benzoyl isothiocyanate (0.33 ml of 0.4 ml in 5 ml of dichloromethane) was added to the product from Example 5.2 (75 mg) in dichloromethane (5 ml) at 0° C. After 1 h, 1,8-diazabicyclo[5.4.0]undec-7-ene (0.06 ml) and methyl iodide (0.1 ml) were added and the solution was stirred at room temperature for 1 h. Chromatography then afforded 1(S)-1-C-[3-(1-benzamido-1-methylthiomethyleneamino)-2-ethoxycarbonyl-4-pyrrolyl]-N-tert-butoxycarbonyl-1,4,5-trideoxy-1,4-imino-2,3-O-isopropylidene-D-ribitol (0.10 g). A solution of this material in methanol (5 ml) saturated with ammonia was heated in a sealed tube at 95° C. for 16 h and then evaporated. Chromatography afforded (1S)-1-C-(2-amino-4-hydroxypyrrolo[3,2-d]pyrimidin-7-yl)-N-tert-butoxycarbonyl-1,4,5-trideoxy-1,4-imino-2,3-O-isopropylidene-D-ribitol (28 mg).

Example 31.2

The product from Example 31.1 (28 mg) was treated as for Example 30.4 above to give (1S)-1-C-(2-amino-4-hydroxypyrrolo[3,2-d]pyrimidin-7-yl)-1,4,5-trideoxy-1,4-imino-D-ribitol hydrochloride salt (16 mg). $^{13}$C NMR (75 MHz, D$_2$O with DCl, d ppm): 156.5 (C), 153.5 (C), 135.8 (C), 131.7 (CH), 114.9 (C), 105.6 (C), 76.7 (C-3), 75.7 (C-2), 63.4 (C-4), 58.1 (C-1), 18.4 (C-5).

Example 32

Preparation of (1S)-1-C-(4-aminopyrrolo[3,2-d]pyrimidin-7-yl)-1,4-dideoxy-1,4-imino-D-ribitol hydrochloride salt

Example 32.1

A solution of the product from Example 1.3 (0.15 g) in methanol (5 ml) containing aminoacetonitrile (0.12 g) and sodium acetate (0.20 g) was heated under reflux for 4 h and then concentrated. Chromatography afforded 1(S)-N-tert-butoxycarbonyl-5-O-tert-butyldimethylsilyl-1-C-[1-cyano-2-cyanomethylamino-ethenyl]-1,4-dideoxy-1,4-imino-2,3-O-isopropylidene-D-ribitol (0.12 g) as a diastereomeric mixture. A solution of this material in dichloromethane (10 ml) containing 1,8-diazabicyclo[5.4.0]undec-7-ene (0.7 ml) and benzyl chloroformate (0.33 ml) was heated under reflux for 1 h. Conventional processing and chromatography afforded (1S)-1-C-(3-amino-1-N-benzyloxycarbonyl-2-cyano-4-pyrrolyl)-N-tert-butoxycarbonyl-5-O-tert-butyldimethylsilyl-1,4-dideoxy-1,4-imino-2,3-O-isopropylidene-D-ribitol (0.125 g).

Example 32.2

A solution of the product from Example 32.1 (0.125 g) in ethanol (10 ml) was stirred in an atmosphere of hydrogen with 10% Pd/C (20 mg) for 0.5 h. The solids were removed, formamidine acetate (0.21 g) was added to the filtrate and the solution was heated under reflux for 16 h and then concentrated. Chromatography of the residue gave (1S)-1-C-(4-aminopyrrolo[3,2-d]pyrimidin-7-yl)-N-tert-butoxycarbonyl-5-O-tert-butyldimethylsilyl-1,4-dideoxy-1,4-imino-2,3-O-isopropylidene-D-ribitol (80 mg).

Example 32.3

The product from Example 32.2 (80 mg) was treated as for Example 30.4 above to give (1S)-1-C-(4-aminopyrrolo[3,2-d]pyrimidin-7-yl)-1,4-dideoxy-1,4-imino-D-ribitol hydrochloride salt (35 mg). $^{13}$C NMR (75 MHz, D$_2$O with DCl, d ppm): 152.1 (C), 146.2 (CH), 140.7 (C), 135.3 (CH), 115.4 (C), 107.7 (C), 76.0 (C-2), 73.1 (C-3), 68.4 (C-4), 61.3 (C-5), 58.3 (C-1).

Example 33

Preparation of (1S)-1-C-(2-amino-4-hydroxypyrrolo[3,2-d]pyrimidin-7-yl)-1,4-dideoxy-1,4-imino-D-ribitol 5-phosphate bis-ammonium salt The product from Example 2.2 (0.13 g) in dry acetonitrile (6 ml) containing tetrazole (0.105 g) was stirred at room temperature while N,N-diethyl-1,5-dihydro-2,4,3-benzodioxaphosphepin-3-amine was added slowly dropwise until t.l.c. indicated complete reaction, then meta-chloroperbenzoic acid (60 mg) was added followed by further small quantities of the oxidant until t.l.c. indicated the initial product was fully reacted. Chloroform was added and the solution was washed with aqueous sodium bicarbonate, dried and concentrated. Chromatography afforded the phosphate ester (190 mg) which was stirred in ethanol (10 ml) in an atmosphere of hydrogen with 10% Pd/C (80 mg) for 1 h. The solids and solvent were removed and the residue was dissolved in trifluoroacetic acid (5 ml) and allowed to stand at room temperature for 16 h. The solution was concentrated by evaporation and the residue in water was applied to a column of Amberlyst A15 acid resin. The column was washed with water and then with 2M aqueous ammonia to elute the product. Concentration and trituration of the residue with water afforded (1S)-1-C-(2-amino-4-hydroxypyrrolo[3,2-d]pyrimidin-7-yl)-1,4-dideoxy-1,4-imino-D-ribitol 5-phosphate bis-ammonium salt (50 mg), referred to as the 5'-phosphate of compound Ib. $^{13}$C NMR (75 MHz, TFA-D, d ppm): 146.9 (C), 144.0 (C), 127.0 (C), 124.5 (CH), 105.1 (C), 95.6 (C), 66.3 (CHH), 64.0 (CH), 59.2 (CH), 56.2 (CH$_2$), 50.2 (CH).

Example 34

Preparation of (1S)-1,4,5-trideoxy-5-fluoro-1-C-(4-hydroxypyrrolo[3,2-d]pyrimidin-7-yl)-1,4-imino-D-ribitol hydrochloride salt

Example 34.1

To a solution of the product from Example 1.2 (1.48 g) in tetrahydrofuran (10 ml) was added tetrabutylammonium fluoride (6 ml, 1M in THF). After 2 h the solution was evaporated and chromatography of the residue afforded (1S)-N-tert-butoxycarbonyl-1-C-cyanomethyl-1,4-dideoxy-1,4-imino-2,3-O-isopropylidene-D-ribitol (1.15 g). A solution of 0.84 g of this material in dichloromethane (20 ml) containing triethylamine (1.0 ml) was stirred while diethylaminosulfur trifluoride (0.36 ml) was added. After 2 h, methanol (1 ml) was added and the solution was evaporated. Chromatography gave (1S)-N-tert-butoxycarbonyl-1-C-cyanomethyl-1,4,5-trideoxy-5-fluoro-1,4-imino-2,3-O-isopropylidene-D-ribitol (0.36 g).

Example 34.2

The product from Example 34.1 (0.36 g) was treated in the same manner as described for examples 1.3 and then 1.4 and 1.5 above to give (1S)-1-C-(3-amino-1-N-benzyloxycarbonyl-2-ethoxycarbonyl-4-pyrrolyl)-N-tert-butoxycarbonyl-1,4,5-trideoxy-5-fluoro-1,4-imino-2,3-O-isopropylidene-D-ribitol (0.23 g).

Example 34.3

The product from Example 34.2 (0.12 g) was treated as described for examples 1.6 and then 1.7 above to give, after lyophilization, (1S)-1,4,5-trideoxy-5-fluoro-1-C-(4-hydroxypyrrolo[3,2-d]pyrimidin-7-yl)-1,4-imino-D-ribitol hydrochloride salt (43 mg). $^{13}$C NMR (75 MHz, D$_2$O with DCl, d ppm): 146.8 (CH), 132.6 (CH), 83.0 ($J_{C,F}$ 169 Hz, C-5), 76.1 (C-2), 72.7 (C-3), 66.4 ($J_{C,F}$ 18 Hz, C-4), 59.0 (C-1).

Example 35

(1S)-1-C-(3-amino-2-carboxamido-4-pyrrolyl)-1,4-dideoxy-1,4-imino-D-ribitol

Example 35.1

Hydrogen peroxide (0.5 ml) was added dropwise to a solution of the product from Example 32.1 (90 mg) and potassium carbonate (50 mg) in dimethylsulfoxide (1.0 ml). The reaction was stirred for 10 minutes, diluted with water (50 ml), extracted with ethyl acetate (3×20 ml), and the combined organic layers dried and concentrated. Chromatography of the resulting residue afforded (1S)-1-C-(3-amino-2-carboxamido-4-pyrrolyl)-N-tert-butoxycarbonyl-5-O-tert-butyldimethylsilyl-1,4-dideoxy-1,4-imino-2,3-O-isopropylidene-D-ribitol (20 mg).

Example 35.2

A solution of the product from Example 35.1 (20 mg) in trifluoroacetic acid (1 ml) was allowed to stand at room temperature for 16 h. The solvent was removed and the residue in water (20 ml) was washed with dichloromethane (2×5 ml). The aqueous layer was evaporated and chromatography afforded (1S)-1-C-(3-amino-2-carboxamido-4-pyrrolyl)-1,4-dideoxy-1,4-imino-D-ribitol (10 mg). NMR (300 MHz, D$_2$O): $^{13}$C 59.3 (C-4'), 64.0 (C-5'), 67.7 (C-1'), 74.4 (C-3'), 77.6 (C-2'), 113.2 (q), 124.1 (C-5), 126.2 (q), 141.0 (q), and 168.7 (q). HRMS (MH$^+$) calc. for C$_{10}$H$_{17}$N$_4$O$_4$: 257.12498; found: 257.12535.

Example 36

Preparation of (1S)-1,4-dideoxy-1-C-(2,4-dihydroxypyrrolo-[3,2-d]pyrimidin-7-yl)-1,4-imino-D-ribitol

Example 36.1

2,4-Dihydroxy-6-methyl-5-nitropyrimidine (G. N. Mitchell and R. L. McKee, *J. Org. Chem.*, 1974, 39, 176–179) (20 g) was suspended in phosphoryl chloride (200 ml) containing N,N-diethylaniline (20 ml) and the mixture was heated under reflux for 2 h. The black solution was concentrated to dryness and the residue was partitioned between water (600 ml) and ether (150 ml). The aqueous phase was further extracted with ether (150 ml) and the combined organic phases were washed with aqueous sodium bicarbonate and processed conventionally to give 2,4-dichloro-6-methyl-5-nitropyrimidine (23.1 g).

Example 36.2

To a solution of the product of Example 36.1 (17 g) in benzyl alcohol (80 ml) was added a 1.1 M solution of sodium benzylate in benzyl alcohol (199 ml). After 1 h at room temperature, ether (500 ml) was added and the solution was washed with water. The organic phase was dried and concentrated to dryness under high vacuum. The crude residue in dry N,N-dimethylformamide (100 ml) and N,N-dimethylformamide dimethyl acetal (25 ml) was heated at 100° C. for 3 h and then the solution was concentrated to dryness. Trituration of the residue with ethanol and filtration afforded 2,4-dibenzyloxy-6-(2-dimethylaminovinyl)-5-nitropyrimidine as an orange solid (24.5 g)

Example 36.3

Zinc dust (30 g) was added to a solution of the product from Example 36.2 (20 g) in acetic acid (300 ml) with cooling to control the exotherm. The resulting mixture was then stirred for 2 h, filtered, and the filtrate was concentrated to dryness. The residue was partioned between chloroform and aqueous sodium bicarbonate, the organic layer was dried and then concentrated to dryness to give a solid residue of 2,4-dibenzyloxypyrrolo[3,2-d]pyrimidine (15.2 g)

Example 36.4

Sodium hydride (0.5 g, 60% dispersion in oil) was added to a solution of the product from example 36.3 (2.0 g) in tetrahydrofuran (40 ml) followed by tert-butyldimethylsilyl chloride (1.37 g) and the mixture was stirred for 1 h. The reaction was quenched with dropwise addition of water and then partitioned between ether (100 ml) and water (150 ml). The organic phase was dried and concentrated to dryness. A solution of the residue in dichloromethane (40 ml) was stirred while N-bromosuccinimide added slowly poritonwise until t.l.c. analysis indicated complete conversion to a less polar product. The solution was washed with water, aqueous sodium bicarbonate, dried and concentrated. Chromatography of the residue afforded 2,4-dibenzyloxy-7-bromo-9-N-tert-butyldimethylsilylpyrrolo[3,2-d]pyrimidine as a white solid (1.8 g).

Example 36.5

An imine was prepared from 5-O-tert-butyldimethylsilyl-1,4-dideoxy-1,4-imino-2,3-O-isopropylidene-D-ribitol (0.30 g) by N-chlorination with N-chlorosuccinimide followed by elimination of hydrogen chloride with lithium tetramethylpiperidide as described in Example 1.1, but with the following modifications: (i) when addition of the solution of lithium tetramethylpiperidide was complete, petroleum ether was added and the solution was washed with water, dried and concentrated to dryness; (ii) the residue was chromatographed on silica gel eluted with 0.2% triethylamine and 30% ethyl acetate in hexanes to afford the pure imine (0.215 g). A solution of this imine in ether (2 ml) was added to a solution prepared by slow addition of butyllithium (1.4 M in hexanes) to a solution of the product from Example 36.4 (0.786 g) in anisole (20 ml) and ether (30 ml) at −70° C. until t.l.c. analysis indicated lithium exchange with the starting material was complete. The mixture was allowed to slowly warm to ~15° C., and then was washed with water, dried and concentrated. Chromatography of the residue afforded (1S)-1-C-)2,4-dibenzyloxy-9-N-tert-butyldimethylsilylpyrrolo[3,2-d]pyrimidin-7-yl)-5-O-tert-butyldimethylsilyl-1,4-dideoxy-1,4-imino-2,3-O-isopropylidene-D-ribitol (0.225 g).

Example 36.6

A solution of the product from Example 36.5 (0.10 g) in ethanol (5 ml) was stirred in a hydrogen atmosphere with 10% palladium on charcoal (0.05 g) for 2 h. The solids and solvent were removed and concentrated aqueous hydrochloric acid (1 ml) was added to a solution of the residue in methanol (5 ml). After standing overnight, the solution was concentrated to dryness and the residue was extracted with ether and then triturated with ethanol and filtered to give (1S)-1,4-dideoxy-1-C-)2,4-dihydroxypyrrolo[3,2-d][pyrimidin-7-yl)-1,4-imino-D-ribitol hydrochloride (0.025 g). $^{13}$C NMR ($D_2O$), δ (ppm): 159.8 (C), 155.8 (C), 137.1 (C), 131.4 (CH), 114.2 (C), 104.1 (C), 76.2 (CH), 73.7 (CH), 68.5 (CH) 61.6 ($CH_2$) and 58.5 (CH).

Example 37

Preparation of 1,4-dideoxy-(1S)-1-C-(2,4-dihydroxypyrrolo-[3,2-d]pyrimidin-7-yl)-1,4-imino-D-ribitol 5-phosphate bis-ammonium salt

Example 37.1

A solution tetrabutylammonium fluoride (1 M, 0.5 ml) was added to a solution of the bis-silylated product from Example 36.5 (110 mg) in tetrahydrofuran. After 2 h, the solution was diluted with toluene, washed with water (×2), dried, and evaporated to dryness. The resulting syrup was dissolved in methanol and tert-butoxycarbonic anhydride (65 mg) was added. After 30 min, the reaction mixture was concentrated to dryness and subjected to chromatography to give (1S)-1-C-(2,4-dibenzyloxypyrrolo[3,2-d]pyrimidin-7-yl)-N-tert-butoxycarbonyl-1,4-dideoxy-1,4-imino-2,3-O-isopropylidene-D-ribitol (64 mg).

Example 37.2

The product for Example 37.2 (64 mg) was converted by the method detailed in Example 33 into, 1,4-dideoxy-(1S)-1-C-(2,4-dihydroxypyrrolo[3,2-d]pyrimidin-7-yl)-1,4-imino-D-ribitol 5-phosphate bis-ammonium salt (11 mg); $^{13}$C-NMR ($D_2O$), δ (ppm): 156.0 (C), 151.9 (C), 134.0 (C), 127.3 (CH), 110.9 (C), 102.8 (C), 75.1 (CH), 70.4 (CH), 65.1 (CH), 61.9 ($CH_2$), and 54.5 (CH).

Aspects of the invention have been described by way of example only and it should be appreciated that modifications and additions thereto may be made without departing from the scope of the invention.

What is claimed is:

1. A pharmaceutical composition comprising (1S)-1,4-dideoxy-1-C-(4-hydroxypyrrolo[3,2-d]pyrimidin-7-yl)-1,4-imino-D-ribitol, or tautomer thereof, or a pharmaceutically acceptable salt thereof.

2. A pharmaceutical composition comprising (1S)-1-C-(2-amino-4-hydroxypyrrolo[3,2-d]pyrimidin-7-yl)-1,4-dideoxy-1,4-imino-D-ribitol, or tautomer thereof, or a pharmaceutically acceptable salt thereof.

* * * * *

UNITED STATES PATENT AND TRADEMARK OFFICE
CERTIFICATE OF CORRECTION

PATENT NO. : 6,492,347 B2
DATED : December 10, 2002
INVENTOR(S) : Richard Hubert Furneaux, Peter Charles Tyler and Vern L. Schramm It is certified that error appears in the above-identified patent and that said Letters Patent is hereby corrected as shown below:

Column 1,
Line 12, please add the following paragraph:

-- STATEMENT OF GOVERNMENT SUPPORT

This invention disclosed herein was made with U.S. Government support under grant number GM41916 from the National Institutes of Health, U.S. Department of Health and Human Services. Accordingly, the U.S. Government has certain rights in this invention. --.

Signed and Sealed this

Sixth Day of September, 2005

JON W. DUDAS
*Director of the United States Patent and Trademark Office*